US011383232B2

(12) United States Patent
Liu et al.

(10) Patent No.: US 11,383,232 B2
(45) Date of Patent: Jul. 12, 2022

(54) SAMPLE TESTING DEVICE, SAMPLE ANALYZER AND SAMPLE TESTING METHOD

(71) Applicant: SHENZHEN MINDRAY BIO-MEDICAL ELECTRONICS CO., LTD., Shenzhen (CN)

(72) Inventors: Yinming Liu, Shenzhen (CN); Jin Teng, Shenzhen (CN); Huilin Shi, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 145 days.

(21) Appl. No.: 16/801,069

(22) Filed: Feb. 25, 2020

(65) Prior Publication Data

US 2020/0188905 A1 Jun. 18, 2020

Related U.S. Application Data

(63) Continuation of application No. PCT/CN2017/100046, filed on Aug. 31, 2017.

(51) Int. Cl.
*B01L 3/00* (2006.01)
*G01N 1/14* (2006.01)
(Continued)

(52) U.S. Cl.
CPC ............... *B01L 3/502* (2013.01); *B01L 13/00* (2019.08); *G01N 1/14* (2013.01); *G01N 15/1404* (2013.01);
(Continued)

(58) Field of Classification Search
None
See application file for complete search history.

(56) References Cited

U.S. PATENT DOCUMENTS 4,606,631 A * 8/1986 Anno ................. G01N 15/1404
250/574
5,311,290 A * 5/1994 Olson ................ G01N 15/1404
348/142
(Continued)

FOREIGN PATENT DOCUMENTS

CN 1057339 A 12/1991
CN 101236149 A * 8/2008
(Continued)

OTHER PUBLICATIONS

English translation of CN-101236149-A. (Year: 2008).*

*Primary Examiner* — Matthew D Krcha
(74) *Attorney, Agent, or Firm* — Kory D. Christensen

(57) ABSTRACT

A sample testing device, a sample testing method, and a sample analyze are provided. The sample testing device includes a pipeline assembly, a testing assembly, and a reaction assembly. The pipeline assembly includes a first pipeline and a second pipeline. The testing assembly includes a sample needle which includes a first connection point. The reaction assembly includes a first reaction cell group connected to a second connection point of the first pipeline and a second reaction cell group which communicates with the second pipeline, and the reaction assembly is configured to treat a biological sample to prepare a test liquid. A test liquid in the first reaction cell group flows to the first connection point via the second connection point of the first pipeline, and a test liquid in the second reaction cell group flows to the first connection point via the second pipeline.

30 Claims, 9 Drawing Sheets

(51) Int. Cl.
*G01N 15/14* (2006.01)
*G01N 33/49* (2006.01)
(52) U.S. Cl.
CPC ...... *G01N 33/49* (2013.01); *B01L 2200/0621* (2013.01); *B01L 2200/141* (2013.01); *B01L 2300/0861* (2013.01)

(56) References Cited

U.S. PATENT DOCUMENTS 6,228,652 B1 * 5/2001 Rodriguez ............. G01N 15/14
356/335
2007/0292308 A1 12/2007 Horan et al.

FOREIGN PATENT DOCUMENTS

| | | |
|---|---|---|
| CN | 101236149 A | 8/2008 |
| CN | 101236195 A | 8/2008 |
| CN | 101451989 A | 6/2009 |
| CN | 102539301 A | 7/2012 |
| CN | 102803970 A | 11/2012 |
| CN | 203929784 U | 11/2014 |
| CN | 104297108 A | 1/2015 |
| CN | 204116276 U | 1/2015 |
| CN | 104914031 A | 9/2015 |
| CN | 105784571 A | 7/2016 |
| CN | 206161538 U | 5/2017 |
| JP | 2012184982 A | 9/2012 |

\* cited by examiner

SAMPLE TESTING DEVICE, SAMPLE ANALYZER AND SAMPLE TESTING METHOD

CROSS-REFERENCE TO RELATED APPLICATIONS

This application is a by-pass continuation of Patent Cooperation Treaty Application No. PCT/CN2017/100046, filed on Aug. 31, 2017, the content thereof is hereby incorporated by reference in its entirety.

TECHNICAL FIELD

The application relates to the technical field of medical instruments, in particular to a sample testing device, a sample analyzer, and a sample testing method.

BACKGROUND

The core detection component in the five-Classification blood cell analyzer is a flow chamber. The detection component detects volume of the blood cells and specific features of blood cell content by a light scattering method, and gives cell counting results and various classification results based on these specific features. With the development of reagent system, more signals for specific features can be obtained after treating blood cells by different reagents to find out more abnormal information and provide valuable detecting results for clinic use.

In order to achieve the above object, the reaction system and the testing system are separated into two parts, and each reagent reaction is completed in a separate reaction cell. During measurement, the reactants after the reaction are transported to the flow chamber for detecting, so that there is a risk of direct cross-contamination of the reactants. In prior art, in order to clean residues caused by the sample transportation process, diluent is generally used for flushing and rinsing, and since the adhesion of some reagents is relatively strong, rinsing with common diluent cannot completely remove the residues, and when these residues are encountered during transporting the next sample, the purity of the sample will be affected and so will the measurement results.

SUMMARY

Embodiments of the application provide a sample testing device, a sample analyzer, and a sample testing method.

A sample testing device provided by an embodiment of the application includes a pipeline assembly, a testing assembly, and a reaction assembly.

The pipeline assembly includes a first pipeline and a second pipeline.

The testing assembly includes a sample needle, and the sample needle includes a first connection point.

The reaction assembly includes a first reaction cell group and a second reaction cell group, the first reaction cell group is connected to a second connection point of the first pipeline, the second reaction cell group communicates with the second pipeline, and the reaction assembly is configured to treat a biological sample to prepare a test liquid.

A test liquid in the first reaction cell group flows to the first connection point of the sample needle via the second connection point of the first pipeline, and a test liquid in the second reaction cell group flows to the first connection point of the sample needle via the second pipeline such that the test liquid in the first reaction cell group or the second reaction cell group flows into the sample needle of the testing assembly respectively for detecting.

An embodiment of the application further provides a sample testing method, the sample testing method is performed by using the sample testing device, and the sample testing method includes:

placing a first biological sample and a second biological sample in the first reaction cell group and the second reaction cell group for treating, respectively, so as to prepare a test liquid;

flowing the test liquid in the first reaction cell group to the first connection point of the sample needle via the second connection point of the first pipeline, and detecting, by the testing assembly, the test liquid in the first reaction cell group which flows to the first connection point of the sample needle at a first time; and flowing the test liquid in the second reaction cell group to the first connection point of the sample needle via the second pipeline, and detecting, by the testing assembly, the test liquid in the second reaction cell group which flows to the first connection point of the sample needle at a second time.

The application also provides a sample analyzer, which includes a sampling assembly and a sample testing device. The sampling assembly includes a sampler which is configured to collect a biological sample and move a position above the reaction assembly to dispense the biological samples into the reaction assembly.

In the sample testing device, the sample analyzer and the sample testing method provided by the embodiments of the application, by connecting the first reaction cell group and the second reaction cell group respectively to the first pipeline and the second pipeline, so that the test liquid in the first reaction cell group and the test liquid in the second reaction cell group can be injected into the testing assembly from different pipelines for detecting, and there is no interference with each other, which is advantageous for ensuring the accuracy of test results of the testing assembly.

BRIEF DESCRIPTION OF THE DRAWINGS

In order to illustrate the technical solutions in the application more clearly, a brief introduction to the drawings required for the implementations will be provided below. Obviously, the drawings in the following description are merely some of the implementations of the application, and those of ordinary skill in the art can also obtain other drawings according to these drawings without involving any inventive effort.

DETAILED DESCRIPTION OF EMBODIMENTS

The technical solutions of the embodiments of the present application will be described below clearly and comprehensively in conjunction with the drawings of the embodiments of the application. Clearly, the embodiments described are merely some embodiments of the application and are not all of the possible embodiments. Based on the embodiments given in the application, all other embodiments that would be obtained by those of ordinary skill in the art without expending inventive effort shall all fall within the scope of protection of the application.

Figure 1:
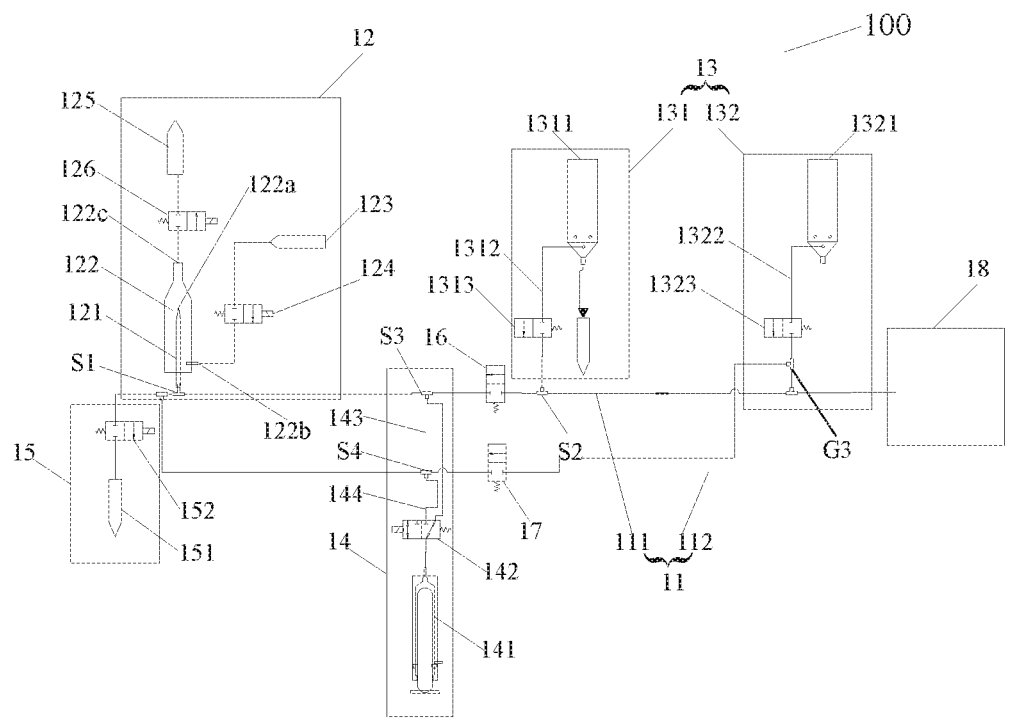
FIG. 1 is a schematic diagram of a sample testing device provided by Embodiment I of the application.

Referring to FIG. 1, Embodiment I of the application provides a sample testing device 100 including a pipeline assembly 11, a testing assembly 12 and a reaction assembly 13. The pipeline assembly 11 is connected between the testing assembly 12 and the reaction assembly 13, and the pipeline assembly 11 is configured for test liquid in the reaction assembly 13 to flow into the testing assembly 12 for detecting.

Referring to FIG. 1, the pipeline assembly 11 includes a first pipeline 111 and a second pipeline 112.

The testing assembly 12 includes a sample needle 121, and the sample needle 121 includes a first connection point S1.

The reaction assembly 13 is configured to treat a biological sample to prepare a test liquid. The reaction assembly 13 includes a first reaction cell group 131 for preparing a first test liquid and a second reaction cell group 132 for preparing a second test liquid, and the first reaction cell group 131 is connected to a second connection point S2 of the first pipeline 111, and the second reaction cell group 132 communicates with the second pipeline 112. The test liquid in the first reaction cell group 131 flows to the first connection point S1 of the sample needle 121 via the second connection point S2 of the first pipeline 111, and the test liquid in the second reaction cell group 132 flows to the first connection point S1 of the sample needle 121 via the second pipeline 112 such that the test liquid in the first reaction cell group 131 or the second reaction cell group 132 respectively flows into the sample needle 121 of the testing assembly 12 for detecting.

Alternatively, the first test liquid and the second test liquid may sequentially flow into the testing assembly 12 for detecting according to a preparation sequence, to increase the testing speed of the sample testing device 100. Of course, in other implementations, the first test liquid and the second test liquid may also sequentially flow into the testing assembly 12 for detecting according to other preset sequences.

Alternatively, the first reaction cell group 131 is configured to prepare the first test liquid for counting leukocytes or classifying leukocytes, and the second reaction cell group 132 is configured to prepare the second test liquid for counting reticulocytes.

The first reaction cell group 131 and the second reaction cell group 132 communicates with the first pipeline 111 and the second pipeline 112, respectively, so that even though the first test liquid in the first reaction cell group 131 and/or the second test liquid in the second reaction cell group 132 is/are prone to adhering to the pipeline wall and difficult to clean, as the first test liquid and the second test liquid can flow via different pipelines (corresponding to the first pipeline 111 and the second pipeline 112 respectively) into the sample needle 121 of the testing assembly 12 for detecting, there is no interference with each other, which is advantageous for ensuring the accuracy of detecting results of the testing assembly 12.

Alternatively, referring to FIG. 1, the first reaction cell group 131 includes a first reaction cell 1311, a first branch 1312, and a first switching member 1313, the first reaction cell 1311 is configured to prepare the first test liquid, the first branch 1312 is connected between the first reaction cell 1311 and the second connection point S2, and the first switching member 1313 is disposed in the first branch 1312, and the first switching member 1313 is configured to implement cutting-off and connecting of the first branch 1312. Specifically, the first switching member 1313 can be a valve.

The flow direction of the first test liquid is specifically described as follows: the first test liquid prepared in the first reaction cell 1311 flows into the first branch 1312, and if the first switching member 1313 is opened, that is, the first switching member 1313 connects the first branch 1312, the first test liquid in the first branch 1312 flows to the second connection point S2, and flows into the first pipeline 111 via the second connection point S2; and if the first switching member 1313 is closed, that is, the first switching member 1313 cuts off the first branch 1312, the first test liquid in the first branch 1312 cannot flow to the second connection point S2, and thus the first test liquid cannot enter the first pipeline 111.

Alternatively, referring to FIG. 1, the second reaction cell group 132 includes a second reaction cell 1321, a second branch 1322, and a second switching member 1323. The second reaction cell 1321 is configured to prepare the second test liquid. One end of the second branch 1322 is connected to the second reaction cell 1321 and the second branch 1322 communicates with the second pipeline 112. The second switching member 1323 is disposed in the second branch 1322. The second switching member 1323 is configured to implement cutting-off and connecting of the second branch 1322. Specifically, the second switching member 1323 can be a valve. The connecting or cutting-off of the second branch 1322 is implemented by opening or closing of the second switching member 1323.

Alternatively, referring to FIGS. 2 to 7, the connecting configurations between the second reaction cell group 132 and the second pipeline 112 are specifically described as follows.

Figure 2:
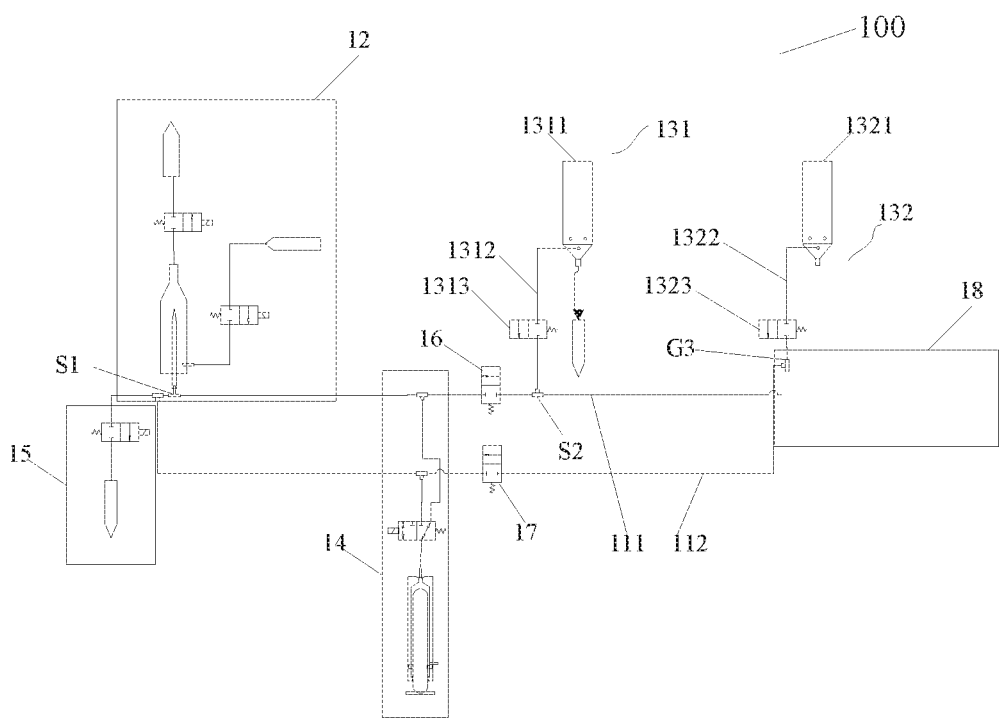
FIGS. 2-7 are schematic diagrams of different connecting configurations of a second pipeline and a second reaction cell group of FIG. 1.

Referring to FIG. 2, as an alternative embodiment, the second pipeline 112 is connected to the second reaction cell group 132, so as to connect the second reaction cell group 132 to the second pipeline 112. Specifically, one end of the second branch 1322 is connected to the second reaction cell 1321, and another end of the second branch 1322 is directly connected to a third end G3 of the second pipeline 112.

Based on the above connecting configuration between the second reaction cell group 132 and the second pipeline 112, the flow direction of the test liquid in the second reaction cell group 132 is specifically described as follows: the second test liquid prepared in the second reaction cell 1321 flows into the second branch 1322, and if the second switching member 1323 is opened, that is, the second switching member 1323 connects the second branch 1322, the second test liquid in the second branch 1322 flows to the third end G3 of the second pipeline 112, and then flows into the second pipeline 112; and if the second switching member 1323 is closed, that is, the second switching member 1323 cuts off the second branch 1322, the second test liquid in the second branch 1322 cannot flow into the second pipeline 112.

The connecting configuration between the second pipeline 112 and the second reaction cell group 132 enables the test liquid in the second reaction cell group 132 to directly flow into the second pipeline 112 without encountering the test liquid in the first reaction cell group 131 which flows into the first pipeline 111, and the connecting configuration of the second pipeline 112 being directly connected to the second reaction cell group 132 has simpler pipeline arrangement and lower costs.

Figure 3:
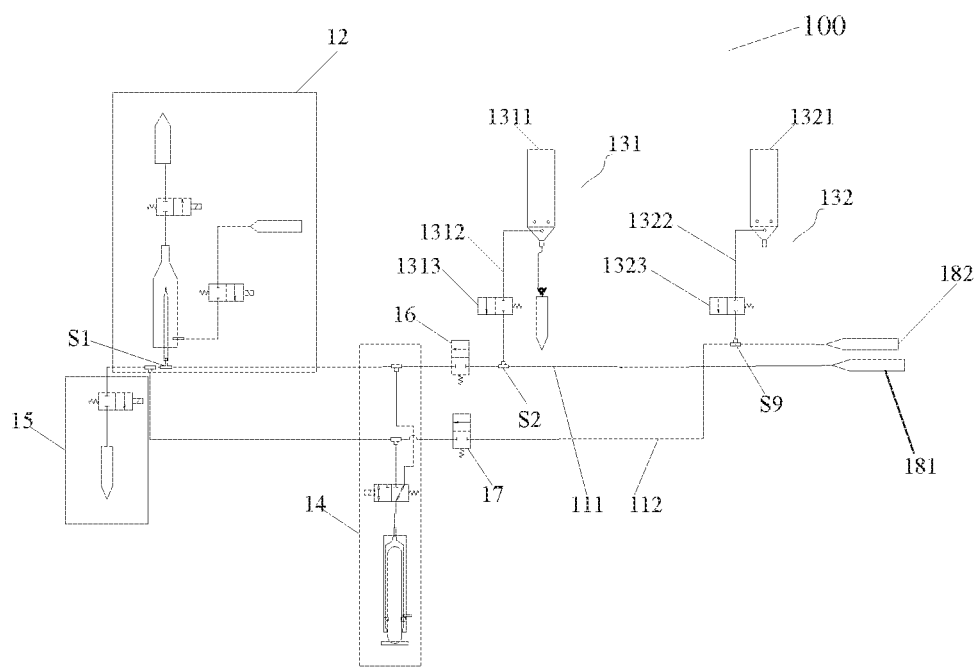

Referring to FIG. 3, as an alternative embodiment, the second reaction cell group 132 is connected to a ninth connection point S9 of the second pipeline 112, and the test liquid in the second reaction cell group 132 flows into the second pipeline 112 from the ninth connection point S9, so as to connect the second reaction cell group 132 to the second pipeline 112. Specifically, one end of the second branch 1322 is connected to the second reaction cell 1321, and another end of the second branch 1322 is connected to the ninth connection point S9 of the second pipeline 112.

Based on the above connecting configuration between the second reaction cell group 132 and the second pipeline 112, the flow direction of the test liquid in the second reaction cell group 132 is specifically described as follows: the second test liquid prepared in the second reaction cell 1321 flows into the second branch 1322, and if the second switching member 1323 is opened, that is, the second switching member 1323 connects the second branch 1322, the second test liquid in the second branch 1322 flows to the ninth connection point S9 of the second pipeline 112, and then flows into the second pipeline 112; and if the second switching member 1323 is closed, that is, the second switching member 1323 cuts off the second branch 1322, the second test liquid in the second branch 1322 cannot flow to the ninth connection point S9.

The connecting configuration between the second pipeline 112 and the second reaction cell group 132 enables the test liquid in the second reaction cell group 132 to directly flow into the second pipeline 112 without encountering the test liquid in the first reaction cell group 131 which flows into the first pipeline 111, and the connecting configuration of the second reaction cell group 132 being directly connected to the second pipeline 112 has simpler pipeline arrangement and lower costs.

Figure 4:
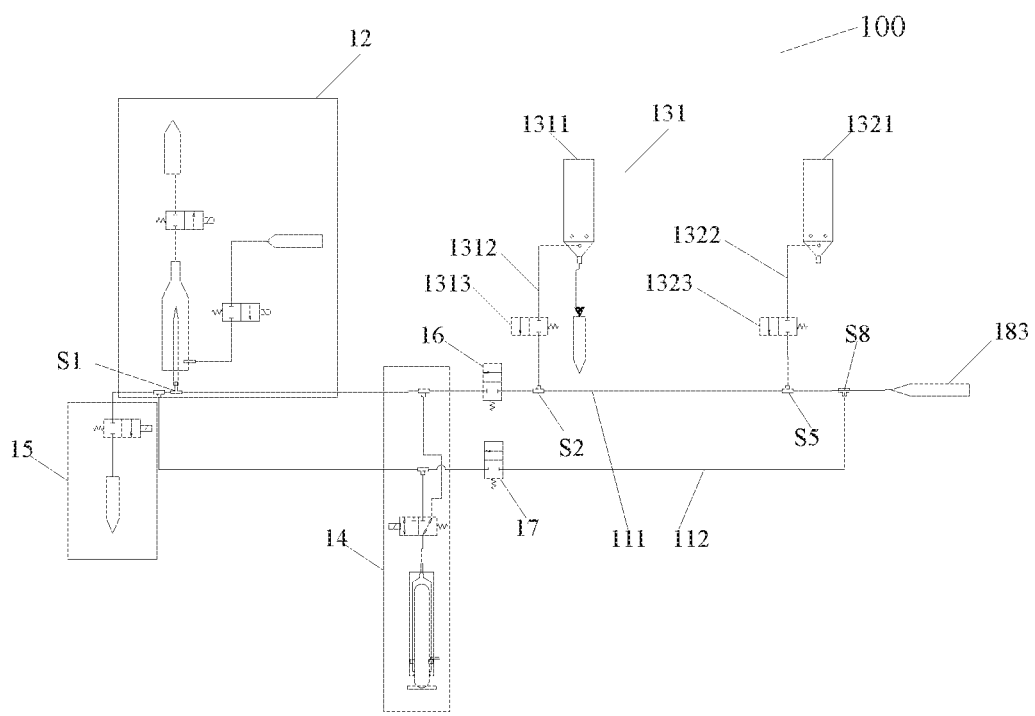
Figure 5:
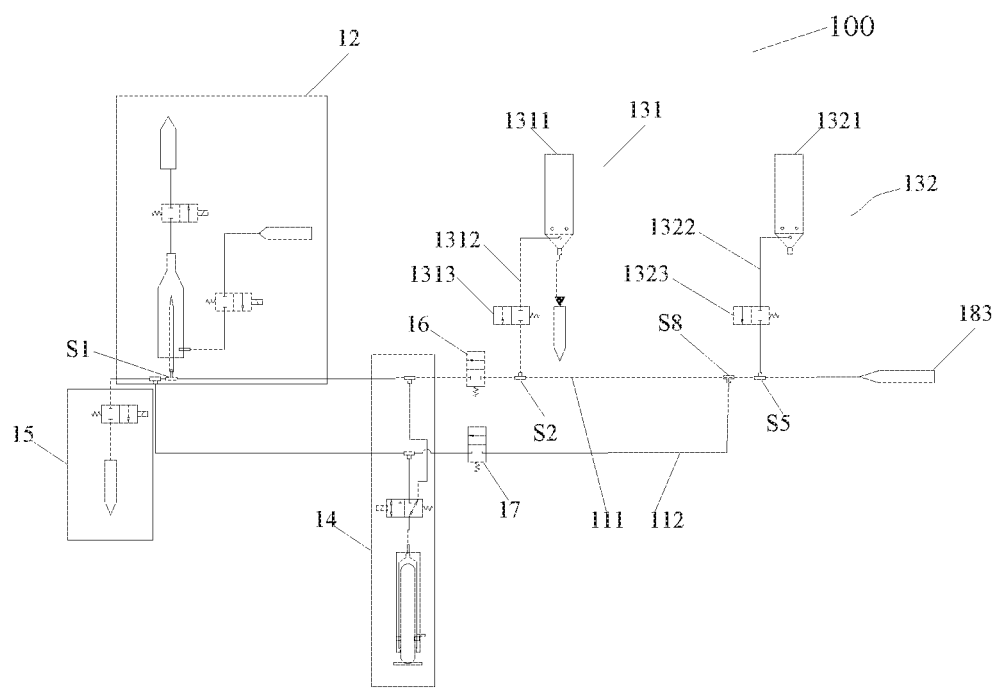

Referring to FIGS. 4 and 5, as an alternative embodiment, the second reaction cell group 132 is connected to the fifth connection point S5 of the first pipeline 111, and one end of the second pipeline 112 is connected to an eighth connection point S8 of the first pipeline 111. Specifically, one end of the second branch 1322 is connected to the second reaction cell 1321, and another end of the second branch 1322 is first connected to a fifth connection point S5 of the first pipeline 111, and the third end of the second pipeline 112 is then connected to the eighth connection point S8 of the first pipeline 111. Here, the fifth connection point S5 and the eighth connection point S8 are farther away from the first connection point S1 than from the second connection point S2, so that while the test liquid in the first reaction cell group 131 is flowing to the first connection point S1 via the second connection point S2, the test liquid in the first reaction cell group 131 does not pass through the fifth connection point S5 and the eighth connection point S8, and therefore when the test liquid in the second reaction cell group 132 first flows via the fifth connection point S5 to the eighth connection point S8 and finally to the second pipeline 112, the test liquid of the second reaction cell group 132 does not encounter the test liquid in the first reaction cell group 131 either.

Alternatively, as illustrated in FIG. 4, the eighth connection point S8 is located on the right side of the fifth connection point S5.

Alternatively, as illustrated in FIG. 5, the eighth connection point is located on the left side of the fifth connection point S5.

Based on the above connecting configuration between the second reaction cell group 132 and the second pipeline 112, the flow direction of the test liquid in the second reaction cell group 132 is specifically described as follows: the second test liquid prepared in the second reaction cell 1321 flows into the second branch 1322, and if the second switching member 1323 is opened, that is, the second switching member 1323 connects the second branch 1322, the second test liquid in the second branch 1322 flows to the fifth connection point S5, and flows from the fifth connection point S5 to the eighth connection point S8 to enter the second pipeline 112 and if the second switching member 1323 is closed, that is, the second switching member 1323 cuts off the second branch 1322, the second test liquid in the second branch 1322 cannot flow to the fifth connection point S5.

Figure 6:
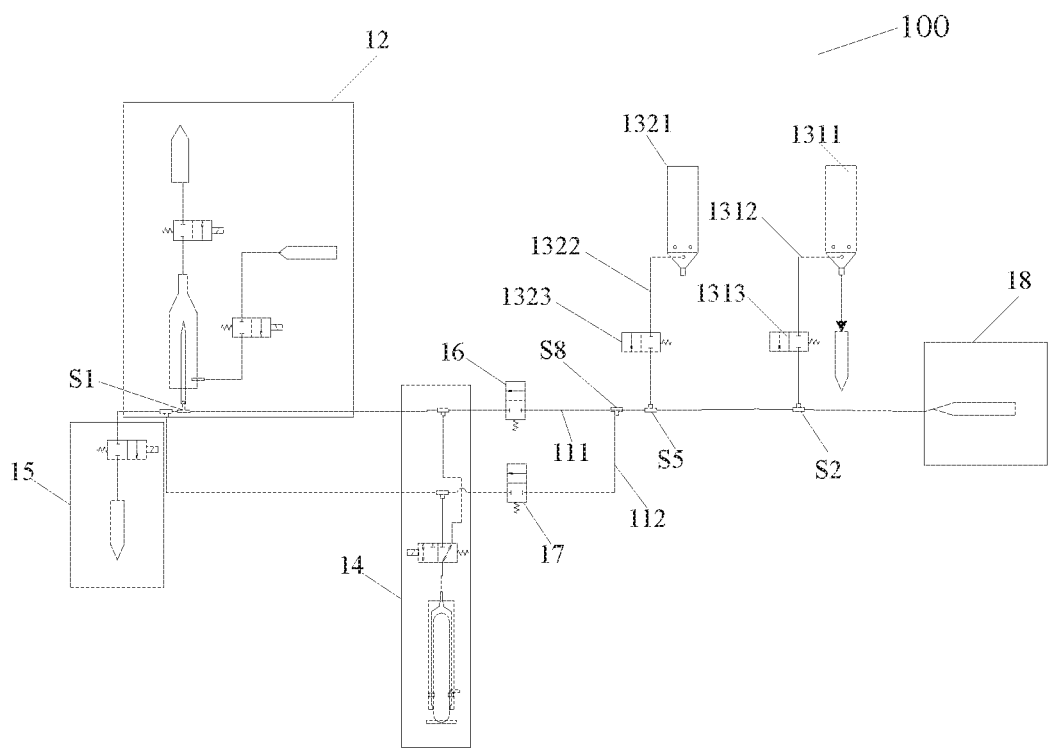

Referring to FIG. 6, as an alternative embodiment, the second reaction cell group 132 is connected to the fifth connection point S5 of the first pipeline 111, and one end of the second pipeline 112 is connected to the eight connection points S8 of the first pipeline 111. Specifically, one end of the second branch 1322 is connected to the second reaction cell 1321, and another end of the second branch 1322 is first connected to the fifth connection point S5 of the first pipeline 111, and the third end G3 of the second pipeline 112 is then connected to the eighth connection point S8 of the first pipeline 111. Here, the fifth connection point S5 and the eighth connection point S8 are closer to the first connection point S1 than the second connection point S2.

Based on the above connecting configuration between the second reaction cell group 132 and the second pipeline 112, the flow direction of the test liquid in the second reaction cell group 132 is specifically described as follows: the second test liquid prepared in the second reaction cell 1321 flows into the second branch 1322, and if the second switching member 1323 is opened, that is, the second switching member 1323 connects the second branch 1322, the second test liquid in the second branch 1322 flows to the fifth connection point S5, and flows from the fifth connection point S5 to the eighth connection point S8 to enter the second pipeline 112; and if the second switching member 1323 is closed, that is, the second switching member 1323 cuts off the second branch 1322, the second test liquid in the second branch 1322 cannot flow to the fifth connection point S5.

Correspondingly, the flow direction of the test liquid in the first reaction cell group 131 is specifically described as follows: the first test liquid prepared in the first reaction cell 1311 flows into the first branch 1312, and if the first switching member 1313 is opened, that is, the first switching member 1313 connects the first branch 1312, the first test liquid in the first branch 1312 flows to the second connection point S2, and flows from the second connection point S2 to the fifth connection point S5 and the eighth connection point S8 sequentially to flow to the first connection point S1. The first test liquid and the second test liquid both flow via the fifth connection point S5 to the eighth connection point S8, but the distance between the fifth connection point S5 and the eighth connection point S8 is shorter, and the cross-contamination brought thereby is almost negligible.

Figure 7:
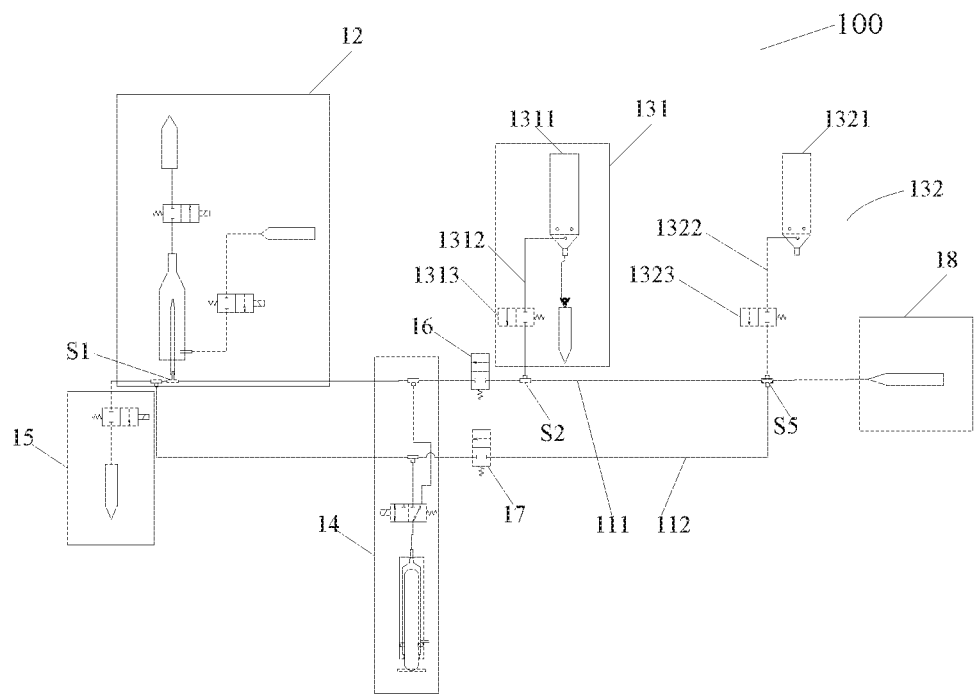

Referring to FIG. 7, as an alternative embodiment, the second pipeline 112 and the second reaction cell group 132 are commonly connected to the fifth connection point S5 of the first pipeline 111, so that the second reaction cell group 132 communicates with the second pipeline 1.12. Specifically, one end of the second branch 1322 is connected to the second reaction cell 1321, and another end of the second branch 1322 and the third end G3 of the second pipeline 112 are both connected to the first pipeline 111 through a four-way joint (i.e., the fifth connection point S5).

Based on the above connecting configuration between the second reaction cell group 132 and the second pipeline 112, the flow direction of the test liquid in the second reaction cell group 132 is specifically described as follows: the second test liquid prepared in the second reaction cell 1321 flows into the second branch 1322, and if the second switching member 1323 is opened, that is, the second switching member 1323 connects the second branch 1322, the second test liquid in the second branch 1322 flows to the fifth connection point S5, and flows from the fifth connection point S5 to the second pipeline 112; and if the second switching member 1323 is closed, that is, the second switching member 1323 cuts off the second branch 1322, the second test liquid in the second branch 1322 cannot flow to the fifth connection point S5.

Alternatively, referring to FIG. 1, the testing assembly 12 further includes a flow chamber 122, a sheath liquid cell 123, a fifth switching member 124, a first waste liquid cell 125, and a sixth switching member 126. The flow chamber 122 has a test liquid inlet 122a, a sheath liquid inlet 122b, and an outlet 122c. The inlet test liquid 122a is connected to the first connection point S1 of the sample needle 121, and the sheath liquid inlet 122b is connected to the sheath liquid cell 123. The sheath liquid cell 123 is configured to store the sheath liquid. The fifth switching member 124 is connected between the sheath liquid cell 123 and the sheath liquid inlet 122b. The fifth switching member 124 is configured to implement cutting-off and connecting of the channel where the fifth switching member is located. The outlet 122c is connected to the first waste liquid cell 125. The sixth switching member 126 is connected between the first waste liquid cell 125 and the outlet 122c. The sixth switching member 126 is configured to implement cutting off and connecting of the channel where the sixth switching member is located. Specifically, the fifth switching member 124 can be a valve. The sixth switching member 126 can be a valve.

Alternatively, the sheath liquid cell 123 is connected to a third gas storage tank, and when the two are in communication with each other, a second positive pressure provided by the third gas storage tank pushes the sheath liquid into the flow chamber 122.

Alternatively, a detection sensor is disposed in the flow chamber 122, and the detection sensor is configured to detect the flow of the test liquid.

Alternatively, the first waste liquid cell 125 is in communication with the atmosphere or a negative pressure.

Referring to FIG. 1, when detection is performed in the flow chamber 122, the test liquid (the first test liquid or the second test liquid) enters the flow chamber 122 from the test liquid 122a inlet. When the fifth switching member 124 is opened, that is, when the fifth switching member connects the sheath liquid cell 123 to the sheath liquid inlet 122b, the sheath liquid in the sheath liquid cell 123 flows into the flow chamber 122 through the sheath liquid inlet 122b, and the sheath liquid surrounds the test liquid to form a test liquid flow for detecting. When the sixth switching member 126 is opened, that is, when the sixth switching member connects the first waste liquid cell 125 to the outlet 122c, the test liquid flow having been detected enters the first waste liquid cell 125 from the outlet 122c.

Alternatively, referring to FIGS. 8 to 10, the connection between the second pipeline 112 and the first connection point S1 of the sample needle 121 is described as follows.

Figure 8:
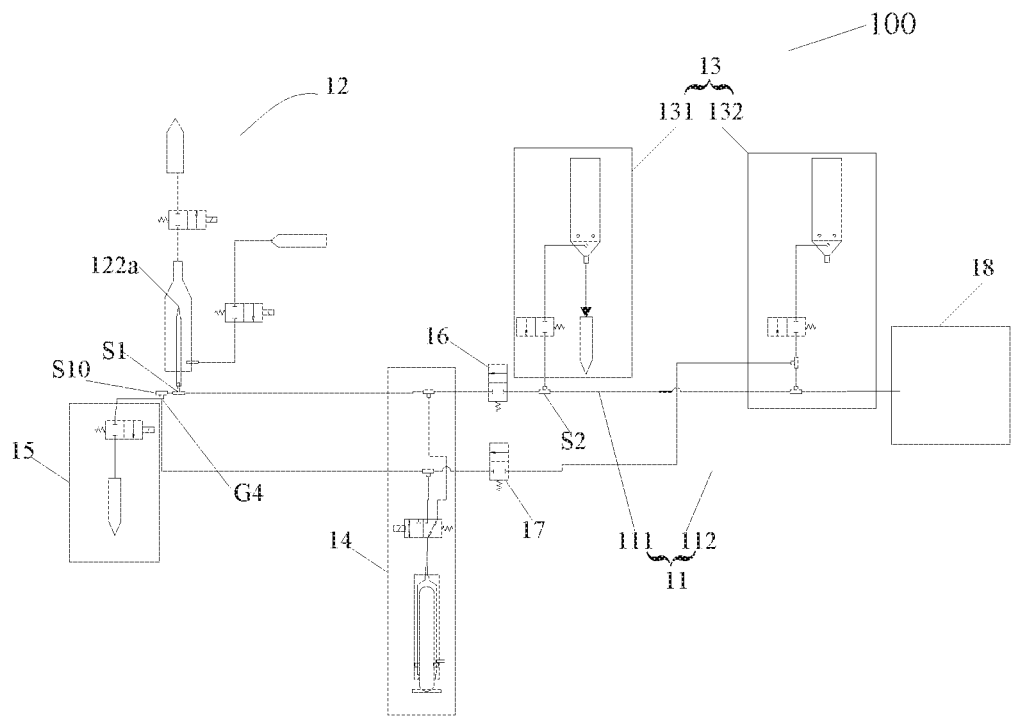
FIGS. 8-10 are schematic diagrams of different connecting configurations of the second pipeline and a first connection point of FIG. 1.

Referring to FIG. 8, as an alternative embodiment, a fourth end G4 of the second pipeline 112 is connected to a tenth connection point S10 of the first pipeline 111, and the tenth connection point S10 communicates with the first connection point S1 of the sample needle 121; and the test liquid in the second reaction cell group 132 flows via the second pipeline 112 to the tenth connection point S10 of the first pipeline 111, and flows to the first connection point S1 of the sample needle 121 from the tenth connection point S10 of the first pipeline 111. It can be understood that, when the test liquid in the first reaction cell group 131 flows from the second connection point S2 of the first pipeline 111 to the first connection point S1 of the sample needle 121, it does not flow through the tenth connection point S10 of the first pipeline 111, thus avoiding cross-contamination with the test liquid of the second reaction cell group 132.

The specific flow direction of the first test liquid in the first pipeline 111 flowing into the testing assembly 12 is as follows: the first test liquid flows from the second connection point S2 to the first connection point S1, and then flows from the first connection point S1 of the sample needle 121 into the test liquid inlet 122a of the flow chamber 122.

The specific flow direction of the second test liquid in the second pipeline 112 flowing into the testing assembly 12 is as follows: the second test liquid flows from the second pipeline 112 to the tenth connection point S10 of the first pipeline 111, and flows from the tenth connection point S10 of the first pipeline 111 to the first connection point S1 of the sample needle 121.

The connecting configuration between the second pipeline 112 and the first connection point S1 of the sample needle 121 in this embodiment is such that the test liquid in the first pipeline 111 and the test liquid in the second pipeline 112 respectively flow into the corresponding pipeline independently from the first reaction cell 1311 and the second reaction cell 1321, and then respectively flow independently to the first connection point S1 of the sample needle 121, and the only cross-contamination for the two test liquids is caused by that they are both required to pass through the first connection point S1 and the sample needle 121 before entering the flow chamber 122 for detecting. It has been proved by experiments that when entering the flow chamber 122 with one common joint, the cross-contamination is not as serious as expected, and in fact, by two pipelines disposed in parallel, the cross-contamination can be largely avoided and product design requirement is thus met, that is, the sample testing device 100 in this embodiment can achieve better effect to avoid cross-contamination by adding a low-cost configuration in which one pipeline and another pipeline are separately provided.

Figure 9:
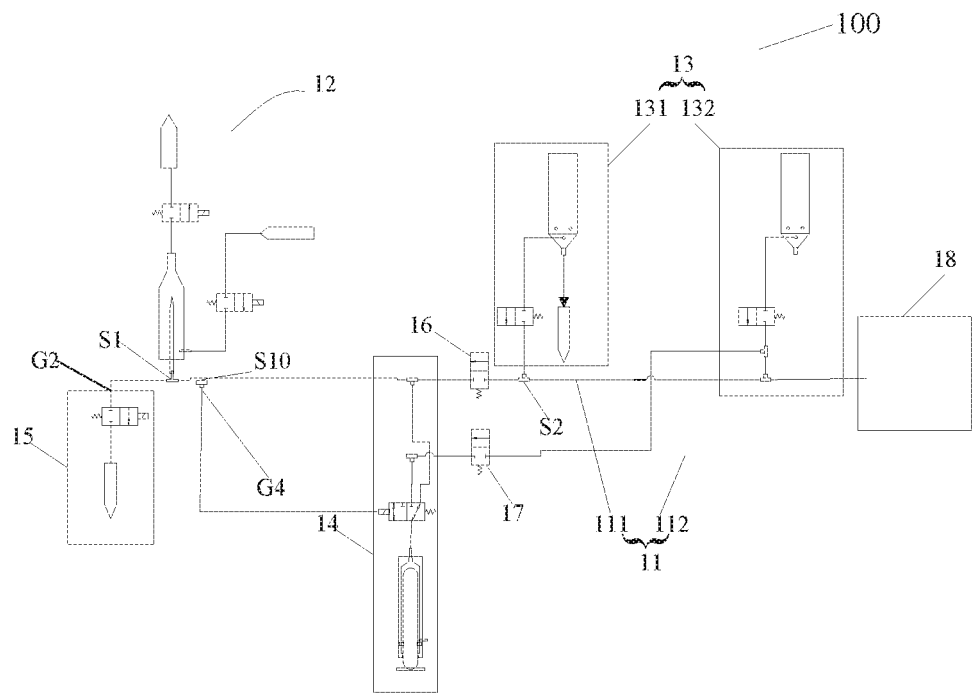

Referring to FIG. 9, as an alternative embodiment, a fourth end G4 of the second pipeline 112 is connected to a tenth connection point S10 of the first pipeline 111, and the tenth connection point S10 communicates with the first connection point S1 of the sample needle 121; and the test liquid in the second reaction cell group 132 flows via the second pipeline 112 to the tenth connection point S10 of the first pipeline 111, and flows to the first connection point S1 of the sample needle 121 from the tenth connection point S10 of the first pipeline 111. It can be understood that, when the test liquid in the first reaction cell group 131 flows from the second connection point S2 of the first pipeline 111 to the first connection point S1 of the sample needle 121, it flows through the tenth connection point S10 in the first pipeline 111. In this alternative embodiment, the tenth connection point S10 is disposed close to the first connection point S1.

The specific flow direction of the first test liquid in the first pipeline 111 flowing into the testing assembly 12 is as follows: the first test liquid flows from the second connection point S2 to the tenth connection point S10, then flows to the first connection point S1, and then flows into the test liquid inlet 122a of the flow chamber 122 from the first connection point S1 of the sample needle 121.

The specific flow direction of the second test liquid in the second pipeline 112 flowing into the testing assembly 12 is as follows: the second test liquid flows from the second pipeline 112 to the tenth connection point S10 of the first pipeline 111, and flows from the tenth connection point S10 of the first pipeline 111 to the first connection point S1 of the sample needle 121.

The connecting configuration between the second pipeline 112 and the first connection point S1 of the sample needle 121 in this embodiment is such that the test liquid in the first pipeline 111 and the test liquid in the second pipeline 112 has a common portion between the tenth connection point S10 and the first connection points S1, and the two test liquids share one joint when entering the flow chamber 122; and it has been proved by experiments that since the tenth connection point S10 is disposed close to the first connection point S1, and the distance between the tenth connection point and the first connection point S1 is very short, so even if the test liquids have a common flow portion and share one joint and the sample needle 121, the cross-contamination is not as serious as expected, and in fact, by two pipelines disposed in parallel, the cross-contamination can be largely avoided and product design requirement is thus met, that is, the sample testing device 100 in this embodiment can achieve better effect to avoid cross-contamination by adding a low-cost configuration in which one pipeline and another pipeline are separately provided.

Figure 10:
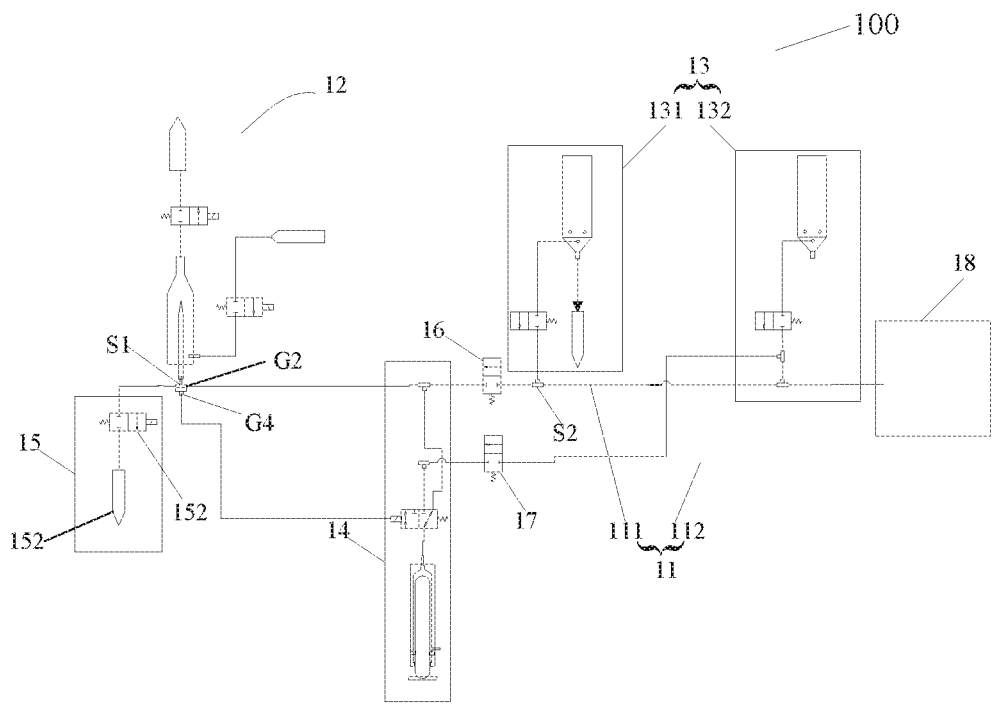

Referring to FIG. 10, as an alternative embodiment, the second pipeline 112 is connected to the first connection point S1 of the testing assembly 12. Specifically, the is fourth end G4 of the second pipeline 112 is directly connected to the first connection point S1 to reduce the flow path of the second test liquid.

Alternatively, the sample needle 121, the first pipeline 111 and the second pipeline 112 communicate with each other via a four-way joint (first connection point S1).

The specific flow direction of the first test liquid in the first pipeline 111 flowing into the testing assembly 12 is as follows: the first test liquid flows from the second connection point S2 to the first connection point S1, and then flows from the first connection point S1 of the sample needle 121 into the test liquid inlet 122a of the flow chamber 122.

The specific flow direction of the second test liquid in the second pipeline 112 flowing into the testing assembly 12 is as follows: the second test liquid flows from the second pipeline 112 to the first connection point S1, and then flows from the first connection point S1 of the sample needle 121 into the test liquid inlet 122a of the flow chamber 122.

The connecting configuration between the second pipeline 112 and the first connection point S1 of the sample needle 121 in this embodiment is such that the test liquid in the first pipeline 111 and the second pipeline 112 respectively flow into the corresponding pipeline independently from the first reaction cell 1311 and the second reaction cell 1321, and then respectively flow independently to the first connection point S1 of the sample needle 121, and the only cross-contamination for the two test liquids is caused by that they are both required to pass through the first connection point S1 and the sample needle 121 before entering the flow chamber 122 for detecting. It has been proved by experiments that when entering the flow chamber 122 with one common joint, the cross-contamination is not as serious as expected, and in fact, by two pipelines disposed in parallel, the cross-contamination can be largely avoided and product design requirement is thus met, that is, the sample testing device 100 in this embodiment can achieve better effect to avoid cross-contamination by adding a low-cost configuration in which one pipeline and another pipeline are separately provided.

Further, referring to FIG. 1, the sample testing device 100 further includes a sample injecting assembly 14, and by providing the sample injecting assembly 14, the test liquid in a first test liquid preparation section or a second test liquid preparation section is injected into the sample needle 121 of the testing assembly 12.

The sample injecting assembly 14 is respectively connected to a third connection point S3 of the first pipeline 111 and a fourth connection point S4 of the second pipeline 112, the third connection point S3 is located between the second connection point S2 and the first connection point S1, a channel between the third connection point S3 and the first connection point S1 is the first test liquid preparation section, and a channel between the fourth connection point S4 and the first connection point S1 is the second test liquid preparation section; the test liquid in the first reaction cell group 131 flows to the third connection point S3 of the first pipeline 111 via the second connection point S2 of the first pipeline 111, and flows into the first test liquid preparation section via the third connection point S3 of the first pipeline 111; and the test liquid in the second reaction cell group 132 flows via the second pipeline 112 to the fourth connection point S4 of the second pipeline 112, and flows into the second test liquid preparation section via the fourth connection point S4 of the second pipeline 112.

Alternatively, referring to FIG. 1, the sample injecting assembly 4 includes an injector 141, a selection switching member 142 disposed at an injection port of the injector 141, a fourth branch 143, and a fifth branch 144. One end of the fourth branch 143 and one end of the fifth branch 144 are respectively connected to the third connection point S3 and the fourth connection point S4, and another end of the fourth branch 143 and another end of the fifth branch 144 are respectively commonly disposed in the selection switching member 142, and the selection switching member 142 is configured to switch between the fourth branch 143 and the fifth branch 144 to communication with the injector 141. Specifically, the selection switching member 142 can be a selection valve.

When the selection switching member 142 is made to communicate with the fourth branch 143, the injection liquid in the injector 141 is injected from the fourth branch 143 to the third connection point S3, so as to inject the first test liquid in the first test liquid preparation section to the first connection point S1 for detecting by the testing assembly 12.

When the selection switching member 142 is made to communicate with the fifth branch 144, the injection liquid in the injector 141 is injected from the fifth branch 144 to the fourth connection point S4, so as to inject the second test liquid in the second test liquid preparation section to the first connection point S1 for detecting by the testing assembly 12.

The selection switching member 142 is disposed such that when the test liquid in the two pipelines of the sample testing device 100 need to flow from the first connection point S1 into the flow chamber 122 for detecting, the selection switching member 142 can be switched according to actual requirements to communicate with the corresponding branch so that the corresponding test liquid can be injected into the flow chamber 122 for detecting.

Further, referring to FIG. 1, the sample testing device 100 further includes a sample drawing assembly 15, the sample drawing assembly 15 is connected to the first pipeline 111 and/or the second pipeline 112, and the sample drawing assembly 15 is configured to generate a negative pressure to correspondingly draw the test liquid in the first reaction cell group 131 into the first test liquid preparation section and/or draw the test liquid in the second reaction cell group 132 into the second test liquid preparation section.

Alternatively, referring to FIG. 1, the sample drawing assembly 15 includes a second waste liquid cell 151 and a seventh switching member 152. A negative pressure is generated in the second waste liquid cell 151. The seventh switching member 152 is connected between the second waste liquid cell 151 and the first pipeline 111 and the second pipeline 112, and the seventh switching member 152 is configured to implement cutting-off and connecting. Specifically, the seventh switching member 152 can be a valve.

Alternatively, the connection manner of the sample drawing assembly 15 in the pipeline assembly 11 is as described follows.

According to the connecting configuration between the second pipeline 112 and the first connection point S1 as illustrated in FIG. 10, referring to FIGS. 1 and 10, as an alternative embodiment, the sample drawing assembly 15 is commonly connected to a second end G2 of the first pipeline 111 and a fourth end G4 of the second pipeline 112. Specifically, the second waste liquid cell 151 is connected to the ends of the first pipeline 111 and the second pipeline 112, a negative pressure is generated in the second waste liquid cell 151, and the seventh switching member 152 is opened to connect the second waste liquid cell 151 to the first pipeline 111 and the second pipeline 112, so as to draw the test liquid in the first pipeline 111 into the first test liquid preparation section and/or draw the test liquid in the second pipeline 112 into the second test liquid preparation section.

In the connecting configuration between the second pipeline 112 and the first connection point S1 as illustrated in FIG. 9, referring to FIGS. 1 and 9, as an alternative embodiment, the sample drawing assembly 15 is connected to the second end G2 of the first pipeline 111. Specifically, the second waste liquid cell 151 is connected to the second end G2 of the first pipeline 111, a negative pressure is generated in the second waste liquid cell 151, and the seventh switching member 152 is opened to connect the second waste liquid cell 151 to the first pipeline 111, so as to draw the test liquid in the first pipeline 111 into the first test liquid preparation section and/or draw the test liquid in the second pipeline 112 into the second test liquid preparation section.

In the connecting configuration between the second pipeline 112 and the first connection point S1 as illustrated in FIG. 8, referring to FIGS. 1 and 8, as an alternative embodiment, the sample drawing assembly 15 is connected to the second pipeline 112. Specifically, the second waste liquid cell 151 is connected to the second pipeline 112, a negative pressure is generated in the second waste liquid cell 151, and the seventh switching member 152 is opened to connect the second waste liquid cell 151 to the second pipeline 112, so as to draw the test liquid in the first pipeline 111 into the first test liquid preparation section and/or draw the test liquid in the second pipeline 112 into the second test liquid preparation section.

It can be understood that, the sample drawing assembly 15 in FIGS. 8 to 10 is correspondingly disposed according to the different connecting configuration between the second pipeline 112 and the first connection point S1, and the manners above are only examples, and do not limit other disposing manners of the sample drawing assembly 15.

Further, referring to FIG. 1, the sample testing device 100 further includes a fourth switching member 16, the fourth switching member 16 is disposed in the first pipeline 111, the fourth switching member 16 is located between the third connection point S3 and the second connection point S2, and the fourth switching member 16 is configured to implement cutting-off and connecting. Specifically, the fourth switching member 16 can be a valve. The cutting-off and connecting between the second connection point S2 and the third connection point S3 is implemented by the fourth switching member 16, so as to control whether the first test liquid in the first reaction cell group 131 can enter the first test liquid preparation section or not.

With the fourth switching member 16 opened, the first test liquid in the first reaction cell group 131 can enter the test liquid first preparation section; and with the fourth switching member 16 closed, the first test liquid in the first reaction cell group 131 cannot enter the first test liquid preparation section.

Further, referring to FIG. 1, the sample testing device 100 further includes an eighth switching member 17, the eighth switching member 17 is disposed in the second pipeline 112, and the eighth switching member 17 is located between the fourth connection point S4 and the third end G3 of the second pipeline 112. The eighth switching member 17 is configured to implement cutting-off and connecting. Specifically, the eighth switching member 17 can be a valve. The cutting-off and connecting of the second pipeline 112 is implemented by the eighth switching member 17, so as to control whether the second test liquid in the second reaction cell group 132 can enter the second test liquid preparation section or not.

With the eighth switching member 17 opened, the second test liquid in the second reaction cell group 132 can enter the second test liquid preparation section; and with the eighth switching member 17 closed, the second test liquid in the second reaction cell group 132 cannot enter the second test liquid preparation section.

Further, referring to FIG. 1, the sample testing device 100 further includes a cleaning assembly 18 for cleaning the pipelines.

Alternatively, the cleaning assembly 18 (a first cleaning assembly 181, a second cleaning assembly 182, and a third cleaning assembly 183) includes a diluent and a cleaning liquid that is stronger than the diluent in cleaning. After each time a biological sample is detected, the pipeline corresponding to the biological sample is cleaned with the diluent to wash the blood sample in the pipeline after reaction. The cleaning action of the cleaning liquid may not be performed for each pipeline, and may be performed for a specific channel, or may be performed for a certain pipeline after the certain pipeline has run for a certain number of times.

As an alternative embodiment, referring to FIG. 3, the sample testing device 100 further includes a first cleaning assembly 181 and a second cleaning assembly 182, the first cleaning assembly 181 is connected to the first pipeline 111, and the cleaning liquid in the first cleaning assembly 181 flows into the first pipeline 111 to clean the first pipeline 111;

and the second cleaning assembly 182 is connected to the second pipeline 112, and the cleaning liquid in the second cleaning assembly 182 flows into the second pipeline 112 to clean the second pipeline 112. Specifically, the first pipeline 111 and the second pipeline 112 are respectively cleaned by their respective cleaning assemblies 18.

As an alternative embodiment, referring to FIG. 4, the sample testing assembly 12 includes a third cleaning assembly 183, and the first pipeline 111 and the second pipeline 112 are commonly connected to the third cleaning assembly 183, the cleaning liquid in the third cleaning assembly 183 flows into the first pipeline 111 to clean the first pipeline 111 and/or flows into the second pipeline 112 to clean the second pipeline 112. Specifically, the cleaning liquid can simultaneously flow into the first pipeline 111 and the second pipeline 112 for cleaning, and the cleaning liquid can also flow into one of the pipelines for cleaning.

As an alternative embodiment, referring to FIG. 5, the third cleaning assembly 183 is connected to an end of the first pipeline 111; the cleaning liquid in the third cleaning assembly 183 flows from the end of the first pipeline 111 into the first pipeline 111 to clean the first pipeline 111; and/or the cleaning liquid in the third cleaning assembly 183 flows from the end of the first pipeline 111 to the fifth connection point S5 of the first pipeline 111, and flows from the fifth connection point S5 to the eighth connection point S8 of the second reaction cell group 132 in the second pipeline 112 to clean the second pipeline 112. Specifically, the cleaning liquid flows into one of the pipelines for cleaning.

The detecting process of the sample testing device 100 is different according to the detecting sequence of the first test liquid and the second test liquid, for example, the first test liquid may be detected firstly, and the second test liquid may be detected secondly. The specific detecting process is as follows.

Referring to FIG. 1, as an alternative embodiment, the detection of the first test liquid is started: opening the first switching member 1313, the fourth switching member 16 and the seventh switching member 152; and after the first test liquid in the first reaction cell 1311 is drawn into the first test liquid preparation section from the second connection point S2 under the negative pressure of the second waste liquid cell 151, closing the first switching member 1313, the fourth switching member 16, and the seventh switching member 152; then, connecting the selection switching member 142 to the fourth branch 143, and injecting the injection liquid in the injector 141 from the fourth branch 143 to the third connection point S3, and injecting the first test liquid in the first test liquid preparation section to the first connection point S1 and then into the flow chamber 122; simultaneously opening the fifth switching member 124 and the sixth switching member 126, so that the first test liquid enters the flow chamber 122 from the test liquid inlet 122a, and the sheath liquid in the sheath liquid cell 123 flows into the flow chamber 122 through the sheath liquid inlet 122b, and the sheath liquid surrounds the first test liquid to form a first test liquid flow for detecting, and finally, the test liquid flow having been detected enters the first waste liquid cell 125 from the outlet 122c; and the detection of the first test liquid is completed.

The detection of the second test liquid is started: opening the second switching member 1323, the eighth switching member 17 and the seventh switching member 152; and after the second test liquid in the second reaction cell 1321 is drawn into the second test liquid preparation section from the second pipeline 112 under the negative pressure of the second waste liquid cell 151, closing the second switching member 1323, the eighth switching member 17 and the seventh switching member 152; then, connecting the selection switching member 142 to the fifth branch 144, and injecting the injection liquid in the injector 141 from the fifth branch 144 to the fourth connection point S4, and injecting the second test liquid in the second test liquid preparation section to the first connection point S1 and then into the flow chamber 122; simultaneously opening the fifth switching member 124 and the sixth switching member 126, so that the second test liquid enters the flow chamber 122 from the test liquid inlet 122a, and the sheath liquid in the sheath liquid cell 123 flows into the flow chamber 122 via the sheath liquid inlet 122b, and the sheath liquid surrounds the second test liquid to form a second test liquid flow for detecting, and finally, the second test liquid having been detected enters the first waste liquid cell 125 from the outlet 122c; and the detection of the second test liquid is completed.

Alternatively, the first switching member 1313, the second switching member 1323, the fourth switching member 16, the eighth switching member 17, and the seventh switching member 152 can be simultaneously opened, so that the first test liquid and the second test liquid simultaneously enter the first test liquid preparation section and the second test liquid preparation section respectively; and then, the selection switching member 142 is switched according to the detection sequence of the first test liquid and the second test liquid, and details are not described herein again.

Alternatively, the second test liquid may be detected first, and then the first test liquid is detected, and the specific process is not described again.

The cleaning processes of the cleaning liquid and the diluent are the same, and the specific rinsing process for rinsing the first pipeline 111 using the cleaning liquid or the diluent is as follows: the fourth switching member 16 and the seventh switching member 152 are opened, and the cleaning liquid or the diluent enters the first pipeline 111 under the coaction of the positive pressure power of the cleaning liquid or the diluent and the negative pressure power of the sample drawing assembly 15 to rinse the first pipeline 111.

The specific rinsing process for rinsing the second pipeline 112 using the cleaning liquid or diluent is as follows: the eighth switching member 17 and the seventh switching member 152 are opened, and the cleaning liquid or the diluent enters the second pipeline 112 under the coaction of the positive pressure power of the cleaning liquid or the diluent and the negative pressure power of the sample drawing assembly 15 to rinse the second pipeline 112.

Figure 11:
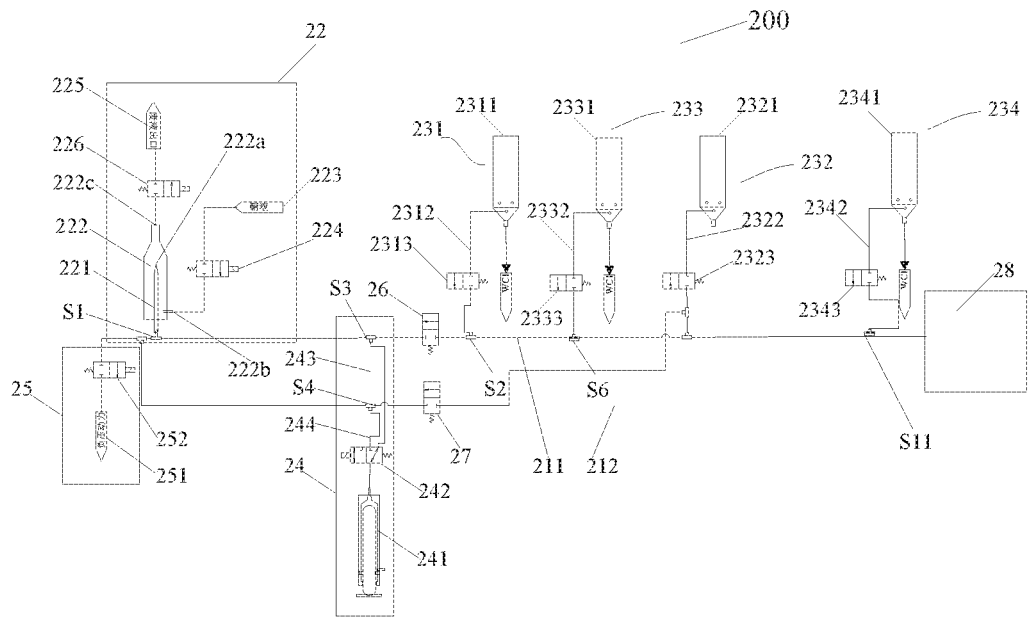
FIG. 11 is a schematic diagram of a sample testing device provided by Embodiment II of the application.

Referring to FIG. 11, Embodiment II of the application further provides a sample testing device 200, the sample testing device 200 is substantially the same as the sample testing device 100 provided in Embodiment I, except that the reaction assembly 23 further includes a third reaction cell group 233 for preparing a third test liquid, the third reaction cell group 233 is connected to a sixth connection point S6 of the first pipeline 211, and the test liquid in the third reaction cell group 233 flows to the first connection point S1 of the sample needle 221 via the sixth connection point S6 of the first pipeline 211, so that the test liquid in the third reaction cell group 233 flows into the sample needle 221 of the testing assembly 22 for detecting.

Alternatively, the first test liquid, the second test liquid, and the third test liquid may sequentially enter the testing assembly 22 according to a preparation sequence, so as to increase the testing speed of the sample testing device 200. Of course, in other implementations, the first test liquid, the second test liquid, and the third test liquid may also enter sequentially the testing assembly 22 for detecting according to other preset sequences.

Alternatively, the first test liquid, the second test liquid, and the third test liquid may sequentially enter the testing assembly 22 according to a preparation sequence, so as to increase the testing speed of the sample testing device 200.

Alternatively, the first test liquid and the third test liquid both flow to the first connection point S1 via the first pipeline 211 for detecting. Therefore, the first test liquid and the third test liquid are test liquids which are proved by experiments to be relatively easy to clean, and thus the accuracy of the detection can be ensured by cleaning the first pipeline 211. The second test liquid is difficult to clean, and is easy to adhere to the pipeline wall, and the independent flow of the second test liquid and the first test liquid can prevent cross-contamination and improve the accuracy of detection.

Alternatively, referring to FIG. 11, the third reaction cell group 233 includes a third reaction cell 2331, a third branch 2332, and a third switching member 2333, the third reaction cell 2331 is configured to prepare a third test liquid, one end of the third branch 2332 is connected to the third reaction cell 2331, and the third branch 2332 communicates with the sixth connection point S6, and the third switching member 2333 is disposed in the third branch 2332, the third switching member 2333 is configured to implement cutting-off and connecting of the third branch 2332.

The flow direction of the third test liquid is specifically as follows; the third test liquid prepared in the third reaction cell 2331 flows into the third branch 2332, and if the third switching member 2333 is opened, that is, the third switching member 2333 connects the third branch 2332, the third test liquid in the third branch 2332 flows to the sixth connection point S6, and flows into the first pipeline 211 via the sixth connection point S6; if the third switching member 2333 is closed, that is, the third switching member 2333 cuts off the third branch 2332, the third test liquid in the third branch 2332 cannot flow to the sixth connection point S6, and thus the third test liquid cannot enter the first pipeline 211.

Since the third reaction cell group 233 and the first reaction cell group 231 are both connected to the first pipeline 211, the corresponding sample injecting assembly 24, sample drawing assembly 25 and cleaning assembly 28 are the same as those in the first embodiment, and are not repeated here. It should be noted that, only one of the third test liquid of the third reaction cell group 233 or the first test liquid in the first reaction cell group 231 can enter the first test liquid preparation section at one time.

The specific detecting process of the sample testing device 200 when detecting the first test liquid, the second test liquid, and the third test liquid is described as follows.

referring to FIG. 11, as an alternative embodiment, the detection of the first test liquid is started: opening the first switching member 2313, the fourth switching member 26 and the seventh switching member 252; after the first test liquid in the first reaction cell 231 is drawn into the first test liquid preparation section from the second connection point S2 under the negative pressure of the second waste liquid cell 251, closing the first switching member 2313, the fourth switching member 26, and the seventh switching member 252; then, connecting the selection switching member 242 to the fourth branch 243, and injecting the injection liquid in the injector 241 from the fourth branch 243 to the third connection point S3, and injecting the first test liquid in the first test liquid preparation section to the first connection point S1 and then into the flow chamber 222; simultaneously opening the fifth switching member 224 and the sixth switching member 226, so that the first test liquid enters the flow chamber 222 from the test liquid inlet 222a, and the sheath liquid in the sheath liquid cell 223 flows into the flow chamber 222 via the sheath liquid inlet 222b, and the sheath liquid surrounds the first test liquid to form a first test liquid flow for detecting, and finally, the test liquid flow having been detected enters the first waste liquid cell 225 from the outlet 222c; and the detection of the first test liquid is completed.

Referring to FIG. 11, the detection of the second test liquid is started: opening the second switching member 2323, the eighth switching member 27, and the seventh switching member 252; and after the second test liquid in the second reaction cell 2321 is drawn into the second test liquid preparation section from the second pipeline 212 under the negative pressure of the second waste liquid cell 251, closing the second switching member 2323, the eighth switching member 27 and the seventh switching member 252; then, connecting the selection switching member 242 to the fifth branch 244, and injecting the injection liquid in the injector 241 from the fifth branch 244 to the fourth connection point S4, and injecting the second test liquid in the second preparation section of test liquid to the first connection point S1 and then into the flow chamber 222; simultaneously, opening the fifth switching member 224 and the sixth switching member 226, so that the second test liquid enters the flow chamber 222 from the test liquid inlet 222a, and the sheath liquid in the sheath liquid cell 223 flows into the flow chamber 222 via the sheath liquid inlet 222b, and the sheath liquid surrounds the second test liquid to form a second test liquid flow for detecting, and finally, the test liquid flow having been detected enters the first waste liquid cell 225 from the outlet 222c; and the detection of the second test liquid is completed.

Referring to FIG. 11, the detection of the third test liquid is started (since the third test liquid and the first test liquid share the first test liquid preparation section, the first pipeline 211 is cleaned by the cleaning assembly 28 before starting the detection, the specific cleaning steps are the same as those mentioned in Embodiment I, and are not described here again): opening the third switching member 2333, the fourth switching member 26 and the seventh switching member 252; and after the third test liquid in the third reaction cell 2331 is drawn from the sixth connection point S6 into the first test liquid preparation section under the negative pressure of the second waste liquid cell 251, closing the third switching member 2333, the fourth switching member 26, and the seventh switching member 252; then, connecting the selection switching member 242 to the fourth branch 243, and injecting the injection liquid in the injector 241 from the fourth branch 243 to the third connection point S3, and injecting the third test liquid in the first test liquid preparation section to the first connection point S1 and then into the flow chamber 222; simultaneously opening the fifth switching member 224 and the sixth switching member 226, so that the third test liquid enters the flow chamber 222 from the test liquid inlet 222a, and the sheath liquid in the sheath liquid cell 223 flows into the flow chamber 222 via the sheath liquid inlet 222b, and the sheath liquid surrounds the third test liquid to form a third test liquid flow for detecting, and finally, the test liquid flow having been detected enters the first waste liquid cell 225 from the outlet 222c; and the detection of the third test liquid is completed.

Alternatively, the first switching member 2313 (or the third switching member 2333), the second switching member 2323, the fourth switching member 26, the eighth switching member 27, and the seventh switching member 252 can be simultaneously opened, so that the first test liquid (or the third test liquid) and the second test liquid simultaneously enter the first test liquid preparation section and the second test liquid preparation section respectively; then, the selection switching member 242 is switched according to the detection sequence of the first test liquid (or the third test liquid) and the second test liquid, and details are not described herein again.

Further, referring to FIG. 11, the sample testing device 200 further includes a fourth reaction cell group 234, and the fourth reaction cell group 234 is connected to an eleventh connection point S11 of the first pipeline 211, and a test liquid in the fourth reaction cell group 234 flows to the first connection point S1 of the sample needle 221 via the eleventh connection point S11 of the first pipeline 211, so that the test liquid in the fourth reaction cell group 234 flows into the sample needle 221 of the testing assembly 22 for detecting.

Alternatively, referring to FIG. 11, the fourth reaction cell group 234 includes a fourth reaction cell 2341, a seventh branch 2342, and an eleventh switching member 2343, and the fourth reaction cell 2341 is configured to prepare a fourth test liquid, one end of the seventh branch 2342 is connected to the fourth reaction cell 2341, and the seventh branch 2342 communicates with the eleventh connection point S11, the eleventh switching member 2343 is disposed in the seventh branch 2342, and the eleventh switching member 2343 is configured to implement cutting-off and connecting of the seventh branch 2342.

Referring to FIG. 11, the flow direction of the fourth test liquid is specifically as follows: the fourth test liquid prepared in the fourth reaction cell 2341 flows into the seventh branch 2342, and if the eleventh switching member 2343 is opened, that is, the eleventh switching member 2343 connects the seventh branch 2342, the fourth test liquid in the seventh branch 2342 flows to the eleventh connection point S11, and flows into the first pipeline 211 via the eleventh connection point S11; if the eleventh switching member 2343 is closed, that is, the eleventh switching member 2343 cuts off the seventh branch 2342, the fourth test liquid in the seventh branch 2342 cannot flow to the eleventh connection point S11, and thus the fourth test liquid cannot enter the first line 211.

Since the fourth reaction cell group 234 is connected to the first pipeline 211, the specific detecting process for detecting the fourth test liquid by the sample testing device 200 is similar to the third test liquid, and the difference is that the flow direction of the fourth test liquid is as described above. Therefore, the specific detecting process of the fourth test liquid is not described here again.

The sample testing device 200 provided y the embodiments of the application can prevent cross-contamination and improve the accuracy of detection by making the second test liquid flow independently from other test liquids.

Figure 12:
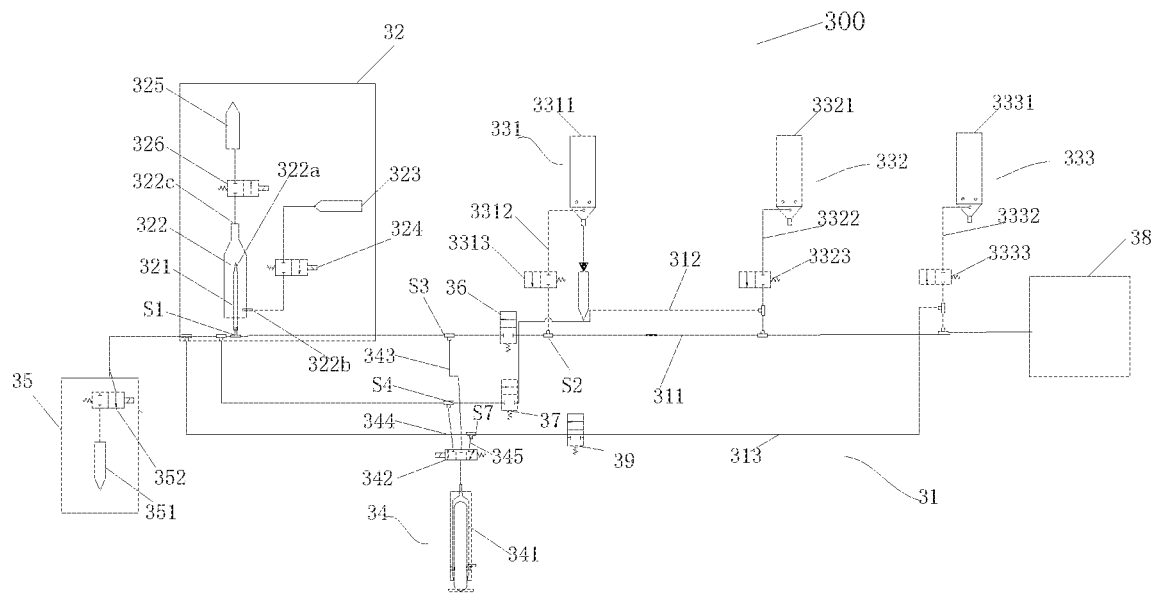
FIG. 12 is a schematic diagram of a sample testing device provided by Embodiment III of the application.

Referring to FIG. 12, Embodiment III of the application further provides a sample testing device 300, and the sample testing device 300 is substantially the same as the sample testing device 100 provided in Embodiment I, except that the pipeline assembly 31 further includes a third pipeline 313, the reaction assembly 33 further includes a third reaction cell group 333, the third reaction cell group 333 communicates with the third pipeline 313. A test liquid in the third reaction cell group 333 flows to the first connection point S1 of the sample needle 321 via the third pipeline 313, so that the test liquid in the third reaction cell group 333 flows into the sample needle 321 of the testing assembly 32 for detecting.

Alternatively, referring to FIG. 12, the third reaction cell group 333 includes a third reaction cell 3331, a third branch 3332, and a third switching member 3333, the third reaction cell 3331 is configured to prepare a third test liquid, one end of the third branch 3332 is connected to the third reaction cell 3331, and the third branch 3332 communicates with the third pipeline 313, and the third switching member 3333 is disposed in the third branch 3332, the third switching member 3333 is configured to implement cutting-off and connecting of the third branch 3332.

The flow direction of the third test liquid is specifically as follows: the third test liquid prepared in the third reaction cell 3331 flows into the third branch 3332, and if the third switching member 3333 is opened, that is, the third switching member 3333 connects the third branch 3332, the third test liquid in the third branch 3332 flows into the third pipeline 313; if the third switching member 3333 is closed, that is, the third switching member 3333 cuts off the third branch 3332, the third test liquid in the third branch 3332 cannot flow into the third pipeline 313, and thus the third test liquid cannot be enter the third pipeline 313.

The first reaction cell group 331, the second reaction cell group 332, and the third reaction cell group 333 communicate respectively with the first pipeline 311, the second pipeline 312 and the third pipeline 313, so that even though the first test liquid in first reaction cell group 331, the second test liquid in the second reaction cell group 332 and/or the third test liquid in the third reaction cell group 333 are prone to adhering to the pipeline wall and difficult to clean, as the first test liquid, the second test liquid and the third test liquid can flow via different pipelines (corresponding to the first pipeline 311, the second pipeline 312 and the third pipeline 313, respectively) into the sample needles 321 of the testing assembly 32 for detecting, there is no interference with each other, which is advantageous for ensuring the accuracy of the detecting results of the testing assembly 32.

Alternatively, for the connecting configuration between the third reaction cell group 333 and the third pipeline 313, reference is made to the connecting configuration between the second reaction cell group 132 and the second pipeline 112 mentioned in Embodiment I, and details are not described herein again.

For the structure of the testing assembly 32, reference is made to the structure of the testing assembly 12 mentioned in Embodiment I, and details are not described herein again.

Referring to FIG. 12, when detection is performed in the flow chamber 322, the test liquid (the first test liquid, the second test liquid, or the third test liquid) enters the flow chamber 322 from test liquid inlet 322*a*; when the fifth switching member 324 is opened, that is, when the fifth switching member connects the sheath liquid cell 323 to the sheath liquid inlet 322*b*, the sheath liquid in the sheath liquid cell 323 flows into the flow chamber 322 via the sheath liquid inlet 322*b*, and the sheath liquid surrounds the test liquid to form a test liquid flow for detecting; and when the sixth switching member 326 is opened, that is, when the sixth switching member connects the first waste liquid cell 325 to the outlet 322*c*, the test liquid flow having been detected enters the first waste liquid cell 325 from the outlet 322*c*.

Alternatively, for the connecting configuration between the third pipeline 313 and the first connection point S1 of the sample needle 321, reference is made to the connecting configuration between the second pipeline 112 and the first connection point S1 of the sample needle 121 mentioned in Embodiment I, and details are not described herein again.

Because the third pipeline 313 is newly added, the sample injecting assembly 34 is configured to inject the test liquid in the first test liquid preparation section, the test liquid in the second test liquid preparation section or the test liquid in the third test liquid preparation section into the sample needle 321 of the testing assembly 32.

Referring to FIG. 12, the sample injecting assembly 34 is respectively connected to the third connection point S3 of the first pipeline 311, the fourth connection point S4 of the second pipeline 312 and the seventh connection point S7 of the third pipeline 313, the third connection point S3 is located between the second connection point S2 and the first connection point S1, a channel between the third connection point S3 and the first connection point S1 is the first test liquid preparation section, a channel between the fourth connection point S4 and the first connection point S1 is the second test liquid preparation section, and a channel between the seventh connection point S7 and the first connection point S1 is the third test liquid preparation section. The test liquid in the first reaction cell group 331 flows to the third connection point S3 of the first pipeline 311 via the second connection point S2 of the first pipeline 311, and flows into the first test liquid preparation section via the third connection point S3 of the first pipeline 311; the test liquid in the second reaction cell group 332 flows to the fourth connection point S4 of the second pipeline 312 via the second pipeline 312, and flows into the second test liquid preparation section via the fourth connection point S4 of the second pipeline 312; the test liquid in the third reaction cell group 333 flows via the third pipeline 313 to the seventh connection point S7 of the third pipeline 313, and flows into the third test liquid preparation section via the seventh connection point S7 of the third pipeline 313.

Alternatively, referring to FIG. 12, the sample injecting assembly 34 includes an injector 341, a selection switching member 342 disposed at an injection port of the injector 341, a fourth branch 343, a fifth branch 344, and a sixth branch 345, and one end of the fourth branch 343, one end of the fifth branch 344, and one end of the sixth branch 345 are respectively connected to the third connection point S3, the fourth connection point S4, and the seventh connection point S7, another end of the fourth branch 343, another end of the fifth branch 344, and another end of the sixth branch 345 are commonly disposed in the selection switching member 342, and the selection switching member 342 is configured to switch between the fourth branch 343, the fifth branch 344, and the sixth branch 345 to communicate with the injector 341. Specifically, the selection switching member 342 can be a selection valve.

When the selection switching member 342 is made to communicate with the fourth branch 343, the injection liquid in the injector 341 is injected from the fourth branch 343 to the third connection point S3, so as to inject the first test liquid in the first test liquid preparation section to the first connection point S1 for detecting by the testing assembly 32.

When the selection switching member 342 is made to communicate with the fifth branch 344, the injection liquid in the injector 341 is injected from the fifth branch 344 to the fourth connection point S4, so as to inject the second test liquid in the second test liquid preparation section to the first connection point S1 for detecting by the testing assembly 32.

When the selection switching member 342 is made to communicate with the sixth branch 345, the injection liquid in the injector 341 is injected from the sixth branch 345 to the seventh connection point S7, so as to inject the third test liquid in the third test liquid preparation section to the first connection point S1 for detecting by the testing assembly 32.

The selection switching member 342 is disposed such that when the test liquid in the three pipelines of the sample testing device 300 needs to flow from the first connection point S1 into the flow chamber 322 for detecting, the switching member 342 can be set according to actual requirements to communicate with the corresponding branch so that the corresponding test liquid can be injected into the flow chamber 322 for detecting.

Correspondingly, referring to FIG. 12, the sample drawing assembly 35 is connected to the first pipeline 311, the second pipeline 312 and/or the third pipeline 313, and the sample drawing assembly 35 is configured to generate a negative pressure to correspondingly draw the test liquid in the first reaction cell group 331 into the first test liquid preparation section, and/or draw the test liquid in the second reaction cell group 332 into the second test liquid preparation section, and/or draw the test liquid in the third reaction cell group 333 into the third test liquid preparation section.

Alternatively, referring to FIG. 12, the sample drawing assembly 35 includes a second waste liquid cell 351 and a seventh switching member 352, a negative pressure is generated in the second waste liquid cell 351, and the seventh switching member 352 is connected between the second waste liquid cell 351 and the first pipeline 311, the second pipeline 312 and the third pipeline 313, and the seventh switching member 352 is configured to implement cutting-off and connecting. Specifically, the seventh switching member 352 can be a valve.

Further, referring to FIG. 12, e sample testing device 300 further includes a fourth switching member 36. For the fourth switching member 36, reference is made to the fourth switching member 16 mentioned in Embodiment I, and details are not described herein again.

Further, referring to FIG. 12, the sample testing device 300 further includes an eighth switching member 37. For the eighth switching member 37, reference is made to the eighth switching member 17 mentioned in Embodiment I, and details are not described herein again.

Further, referring to FIG. 12, since the third pipeline 313 is newly added, the corresponding sample testing device 300 further includes a ninth switching member 39, and the ninth switching member 39 is disposed in the third pipeline 313, the ninth switching member 39 is located between the seventh connection point S7 and the third pipeline 313, and the ninth switching member 39 is configured to implement cutting-off and connecting. Specifically, the ninth switching member 39 can be a valve. The cutting-off and connecting of the third pipeline 313 is implemented by the ninth switching member 39, so as to control whether the third test liquid in the third reaction cell group 333 can enter the third test liquid preparation section or not.

If the ninth switching member 39 is opened, the third test liquid in the third reaction cell group 333 can enter the third test liquid preparation section; and if the ninth switching member 39 is closed, the third test liquid in the third reaction cell group 333 cannot enter the third test liquid preparation section.

Further, referring to FIG. 12, the sample testing device 300 further includes a cleaning assembly 38. For the cleaning assembly 38 in the third pipeline 313, reference is made to the structure of the cleaning assembly 182 in the second pipeline 112 mentioned in Embodiment I, for example, the first pipeline 211, the second pipeline 212, and the third pipeline 313 can respectively communicate with one cleaning assembly 38, and for example, the first pipeline 211, the second pipeline 212, and the third pipeline 313 can commonly communicate with one cleaning component 38, and details are not described herein again.

When the sample testing device 300 detects the first test liquid, the second test liquid and the third test liquid, the following detecting process is applicable.

Referring to FIG. 12, as an alternative embodiment, the detection of the first test liquid is started: opening the first switching member 3313, the fourth switching member 36 and the seventh switching member 352; and after the first test liquid in the first reaction cell 3311 is drawn into the first test liquid preparation section from the second connection point S2 under the negative pressure of the second waste liquid cell 351, closing the first switching member 3313, the fourth switching member 36, and the seventh switching member 352; then, connecting the selection switching member 342 to the fourth branch 343, and injecting the injection liquid in the injector 341 from the fourth branch 343 to the third connection point S3, and injecting the first test liquid in the first test liquid preparation section to the first connection point S1 and then into the flow chamber 322; simultaneously opening the fifth switching member 324 and the sixth switching member 326, so that the first test liquid enters the flow chamber 322 from the test liquid inlet 322a, and the sheath liquid in the sheath liquid cell 323 flows into the flow chamber 322 via the sheath liquid inlet 322b, and the sheath liquid surrounds the first test liquid to form a first test liquid flow for detecting, and finally the test liquid flow having been detected enters the first waste liquid cell 325 from the outlet 322c; and the detection of the first test liquid is completed.

Referring to FIG. 12, the detection of the second test liquid is started: opening the second switching member 3323, the eighth switching member 37, and the seventh switching member 352; and after the second test liquid in the second reaction cell 3321 is drawn into the second test liquid preparation section from the second pipeline 312 under the negative pressure of the second waste liquid cell 351, closing the second switching member 3323, the eighth switching member 37 and the seventh switching member 352; then, connecting the selection switching member 342 to the fifth branch 344, and injecting the injection liquid in the injector 341 from the fifth branch 344 to the fourth connection point S4, and injecting the second test liquid in the second test liquid preparation section to the first connection point S1 and then into the flow chamber 322; simultaneously opening the fifth switching member 324 and the sixth switching member 326, so that the second test liquid enters the flow chamber 322 from the test liquid inlet 322a, and the sheath liquid in the sheath liquid cell 323 flows into the flow chamber 322 via the sheath liquid inlet 322b, and the sheath liquid surrounds the second test liquid to form a second test liquid flow for detecting, and finally the test liquid flow having been detected enters the first waste liquid cell 325 from the outlet 322c; and the detection of the second test liquid is completed.

Referring to FIG. 12, the detection of the third test liquid is started: opening the third switching member 3333, the ninth switching member 39, and the seventh switching member 352; and after the third test liquid in the third reaction cell 3331 is drawn into the third test liquid preparation section from the third pipeline 313 under the negative pressure of the second waste liquid cell 351, closing the third switching member 3333, the ninth switching member 39 and the seventh switching member 352; then, connecting the selection switching member 342 to the sixth branch 345, and injecting the injection liquid in the injector 341 from the sixth branch 345 to the seventh connection point S7, and injecting the third test liquid in the third test liquid preparation section to the first connection point S1 and then into the flow chamber 322; simultaneously opening the fifth switching member 324 and the sixth switching member 326, so that the third test liquid enters the flow chamber 322 from the test liquid inlet 322a, and the sheath liquid in the sheath liquid cell 323 flows into the flow chamber 322 via the sheath liquid inlet 322b, and the sheath liquid surrounds the third test liquid to form a third test liquid flow for detecting, and finally the third test liquid flow having been detected enters the first waste liquid cell 325 from the outlet 322c; and the detection of the third test liquid is completed.

Alternatively, the first switching member 3313, the second switching member 3323, the third switching member 3333, the fourth switching member 36, the eighth switching member 37, the ninth switching 39, and the seventh switching member 352 can be simultaneously opened, so that the first test liquid, the second test liquid and the third test liquid simultaneously enter the first test liquid preparation section, the second test liquid preparation section and the third test liquid preparation section respectively; and then, the selection switching member 342 is switched according to the detection sequence of the first test liquid, the second test liquid and the third test liquid, and details are not described herein again.

Alternatively, after each time a biological sample is detected, the pipeline corresponding to the biological sample is cleaned with the diluent to wash the blood sample in the pipeline after reaction. The cleaning action of the cleaning liquid may not be performed for each pipeline, and may be performed for a specific channel, or may be performed for a certain pipeline after the certain pipeline has run for a certain number of times.

The specific rinsing process for rinsing the first pipeline 311 using a cleaning liquid or diluent is as follows: the fourth switching member 36 and the seventh switching member 352 are opened, and the cleaning liquid or the diluent enters the first pipeline 311 under the coaction of the positive pressure power of the cleaning liquid or the diluent and the negative pressure power of the sample drawing assembly 35 to rinse the first pipeline 311.

The specific rinsing process for rinsing the second pipeline 312 using the cleaning liquid or diluent is as follows: the eighth switching member 37 and the seventh switching member 352 are opened, and the cleaning liquid or the diluent enters the second pipeline 312 under the coaction of the positive pressure power of the cleaning liquid or the diluent and the negative pressure power of the sample drawing assembly 35 to rinse the second pipeline 312.

The specific rinsing process for rinsing the third pipeline 313 using a cleaning liquid or diluent is as follows: the ninth switching member 39 and the seventh switching member 352 are opened, and under the coaction the positive pressure power of the cleaning liquid power or the diluent and the negative pressure power of the sample drawing assembly 35, the cleaning liquid enters the third pipeline 313 to rinse the third pipeline 313.

An embodiment of the application further provides a sample analyzer 1000, the sample analyzer 1000 includes a sampling assembly and a sample testing device described in Embodiment I, Embodiment II or Embodiment III, and the sampling assembly is configured to collect and dispense biological samples. The sample analyzer 1000 is configured to analyze the biological sample. The sampling assembly includes a sampler, the sampler is configured to be capable of collecting a biological sample outside a housing, and then quickly moving to a position above the reaction assembly, and dispensing the biological sample into the reaction assembly for subsequent detection. The sampling assembly includes a sampler, the sampler is configured to collect a biological sample and moves to a position above the reaction assembly, and dispense the biological sample into the reaction assembly for subsequent detection.

Figure 16:
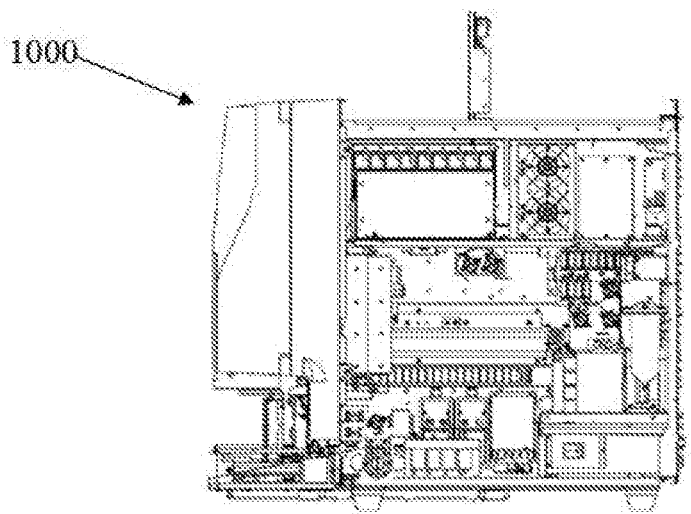
FIG. 16 is a schematic diagram of a sample analyzer of the application.

As can be appreciated, the sample analyzer 100 further includes a housing, the housing includes an operating end (left side of FIG. 16), the first reaction cell group and the third reaction cell group are arranged closer to the operating end compared to the second reaction cell group.

The sample testing device 300 provided by the embodiment of the application enables the first test liquid, the second test liquid, and the third test liquid to flow via different pipelines (corresponding to the first pipeline 311 and the second pipeline 312, the third pipeline 313, respectively) into the sample needle 321 of the testing assembly 32 for detecting, so that there is no interference with each other, which is advantageous for ensuring the accuracy of the detecting results of the testing assembly 32.

Figure 13:
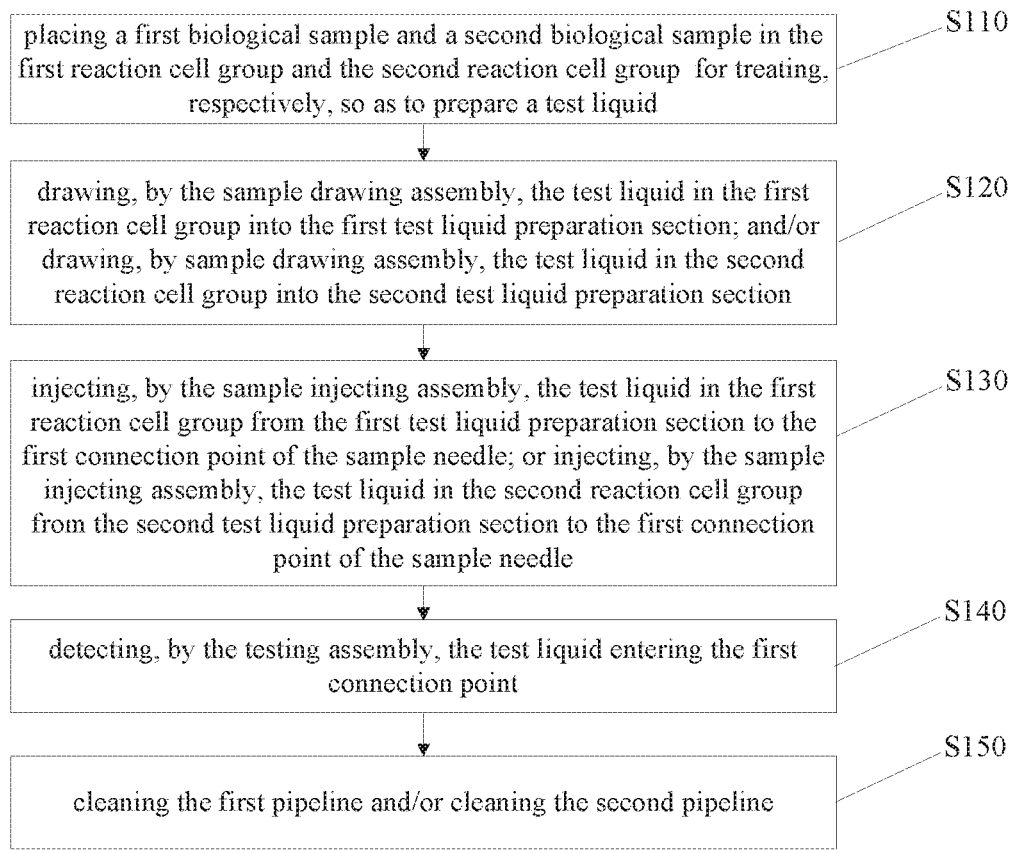
FIG. 13 is a flowchart of a sample testing method provided by an embodiment of the application.

Referring to FIGS. 1 and 13, an embodiment of the application further provides a sample testing method, the sample testing method is performed by using the sample testing device 100 provided by Embodiment I, and the sample testing method includes steps 110-150.

S110: placing a first biological sample and a second biological sample in the first reaction cell group 131 and the second reaction cell group 132 for treating, respectively, so as to prepare a test liquid.

Alternatively, the first biological sample is different from the second biological sample. For example, the first reaction cell group 131 is capable of being configured to prepare a first test liquid for counting leukocytes, and the second reaction cell group 132 is capable of being configured to prepare a second test liquid for counting reticulocytes.

S120: drawing, by the sample drawing assembly 15, the test liquid in the first reaction cell group 131 into the first test liquid preparation section; and/or drawing, by sample drawing assembly 15, the test liquid in the second reaction cell group 132 into the second test liquid preparation section.

Specifically, when drawing the first test liquid and the second test liquid sequentially: the first switching member 1313, the fourth switching member 16 and the seventh switching member 152 are opened; after the first test liquid in the first reaction cell 1311 is drawn into the first test liquid preparation section from the second connection point S2 under the negative pressure of the second waste liquid cell 151, the first switching member 1313, the fourth switching member 16, and the seventh switching member 152 are closed. The drawing of the second test liquid first is not to be described here again.

When drawing the first test liquid and the second test liquid simultaneously, the first switching member 1313, the fourth switching member 16, the second switching member 1232, the eighth switching member 17 and the seventh switching member 152 are opened, so that the first test liquid in the first reaction cell 1311 is drawn into the first test liquid preparation section from the second connection point S2 under the negative pressure of the second waste liquid cell 151, and the second test liquid in the second reaction cell 1321 is drawn into the second test liquid preparation section from the second pipeline 112 under the negative pressure of the second waste liquid cell 151.

The above two drawing situations are correspondingly performed according to actual needs, after the drawing of the test liquid is completed, the opened switching member is closed for subsequent operations.

S130: injecting, by the sample injecting assembly 14, the test liquid in the first reaction cell group 131 from the first test liquid preparation section to the first connection point S1 of the sample needle 121; or injecting, by the sample injecting assembly 14, the test liquid in the second reaction cell group 132 from the second test liquid preparation section to the first connection point S1 of the sample needle 121.

Specifically, the first test liquid or the second test liquid is injected to the first connection point S1 according to actual requirements, the process of injecting the first test liquid to the first connection point S1 is as follows: the selection switching member 142 is made to communicate with the fourth branch 143, and the injection liquid in the injector 141 is injected from the fourth branch 143 to the third connection point S3, and the first test liquid in the first test liquid preparation section is injected to the first connection point S1 to enter the flow chamber 122.

The process of injecting the second test liquid to the first connection point S1 is as follows: the selection switching member 142 is made to communicate with the fifth branch 144, and the injection liquid in the injector 141 is injected from the fifth branch 144 to the fourth connection point S4, and the second test liquid in the second test liquid preparation section is injected to the first connection point S1 to enter the flow chamber 122.

S140: detecting, by the testing assembly 12, the test liquid entering the first connection point S1.

Specifically, if the sample injecting assembly 14 injects the test liquid in the first reaction cell group 131 from the first test liquid preparation section to the first connection point S1 of the sample needle 121 in S130, the first test liquid is detected at a first time as follows: opening the fifth switching member 124 and the sixth switching member 126, so that the first test liquid enters the flow chamber 122 from the test liquid inlet 122a, and the sheath liquid in the sheath liquid cell 123 flows into the flow chamber 122 through the sheath liquid inlet 122b, and the sheath liquid surrounds the first test liquid to form a first test liquid flow for detecting, and finally the test liquid flow having been detected enters the first waste liquid cell 125 from the outlet 122c, and the detection of the first test liquid is completed.

If the sample injecting assembly 14 injects the test liquid in the second reaction cell group 132 from the second test liquid preparation section to the first connection point S1 of the sample needle 121 in S130, the second test liquid is detected at a second time as follows: opening the fifth switching member 124 and the sixth switching member 126, so that the second test liquid enters the flow chamber 122 from the test liquid inlet 122a, and the sheath liquid in the sheath liquid cell 123 flows into the flow chamber 122 via the sheath liquid inlet 122b, and the sheath liquid surrounds the second test liquid to form a second test liquid flow for detecting, and finally the second test liquid flow having been detected enters the first waste liquid cell 125 from the outlet 122c, and the detection of the second test liquid is completed.

The above first time is different from the second time, that is, the testing assembly 12 detects the first test liquid and the second test liquid at different times respectively (time sharing).

S150: cleaning the first pipeline 111 and/or cleaning the second pipeline 112.

Alternatively, the cleaning assembly 18 (the first cleaning assembly 181, the second cleaning assembly 182, and the third cleaning assembly 183) includes a diluent and a cleaning liquid that is stronger than the diluent in cleaning. After each time a biological sample is detected, the pipeline corresponding to the biological sample is cleaned with the diluent to wash the blood sample in the pipeline after reaction. The cleaning action of the cleaning liquid may not be performed for each pipeline, and may be performed for a specific channel, or may be performed for a corresponding pipeline after detecting once, or may be performed for a certain pipeline after the certain pipeline has run for a certain number of times. For example, the first pipeline may be cleaned with the cleaning liquid after detecting the first test liquid, or the first pipeline may be cleaned with the cleaning liquid after the first pipeline has run for multiple detection times accumulatively; and the second pipeline may be cleaned with the cleaning liquid after detecting the second test liquid, or the second pipeline may be cleaned with the cleaning liquid after the second pipeline has run for multiple detection times accumulatively.

The cleaning processes of the cleaning liquid and the diluent are the same, and the specific rinsing process for rinsing the first pipeline 111 using the cleaning liquid or the diluent is as follows: the fourth switching member 16 and the seventh switching member 152 are opened, and the cleaning liquid or the diluent enters the first pipeline 111 under the coaction of the positive pressure power of the cleaning liquid or the diluent and the negative pressure power of the sample drawing assembly 15 to rinse the first pipeline 111.

The specific rinsing process for rinsing the second pipeline 112 using the cleaning liquid or diluent is as follows: the eighth switching member 17 and the seventh switching member 152 are opened, and the cleaning liquid or the diluent enters the second pipeline 112 under the coaction of the positive pressure power of the cleaning liquid or the diluent and the negative pressure power of the sample drawing assembly 15 to rinse the second pipeline 112.

If the first test liquid and the second test liquid are sequentially detected, after the first test liquid and the second test liquid are both detected for once or cumulative times, the first pipeline 111 and the second pipeline 112 are cleaned with the cleaning liquid.

The sample testing device 100 further includes a controller, and the controller is configured to count the statistics times that the testing assembly 12 detects the test liquid in the first reaction cell group 131 and the test liquid in the second reaction cell group 132, respectively, and determine whether the statistics times reach the preset detection amount. When a cleaning strategy is to clean the corresponding pipeline after detecting certain times accumulatively (that is, after the corresponding pipeline has run for a certain number of times accumulatively), the testing assembly 12 cleans the first pipeline 111 with the cleaning liquid after performing a preset detection amount on the test liquid in the first reaction cell group 131; and/or, the testing assembly 12 cleans the second pipeline 112 with the cleaning liquid after performing a preset detection amount on the test liquid in the second reaction cell group 132.

The sample testing method provided by the embodiment of the application enables the first reaction cell group 131 and the second reaction cell group 132 to communicate with the first pipeline 111 and the second pipeline 112, respectively, so that even though the first test liquid in the first reaction cell group 131 and/or the second test liquid in the second reaction cell group 132 is/are prone to adhering to the pipeline wall and difficult to clean, as the first test liquid and the second test liquid can flow via different pipelines (corresponding to the first pipeline 111 and the second pipeline 112 respectively) into the sample needle 121 of the testing assembly 12 for detecting, there is no interference with each other, which is advantageous for ensuring the accuracy of the detecting results of the testing assembly 12.

Figure 14:
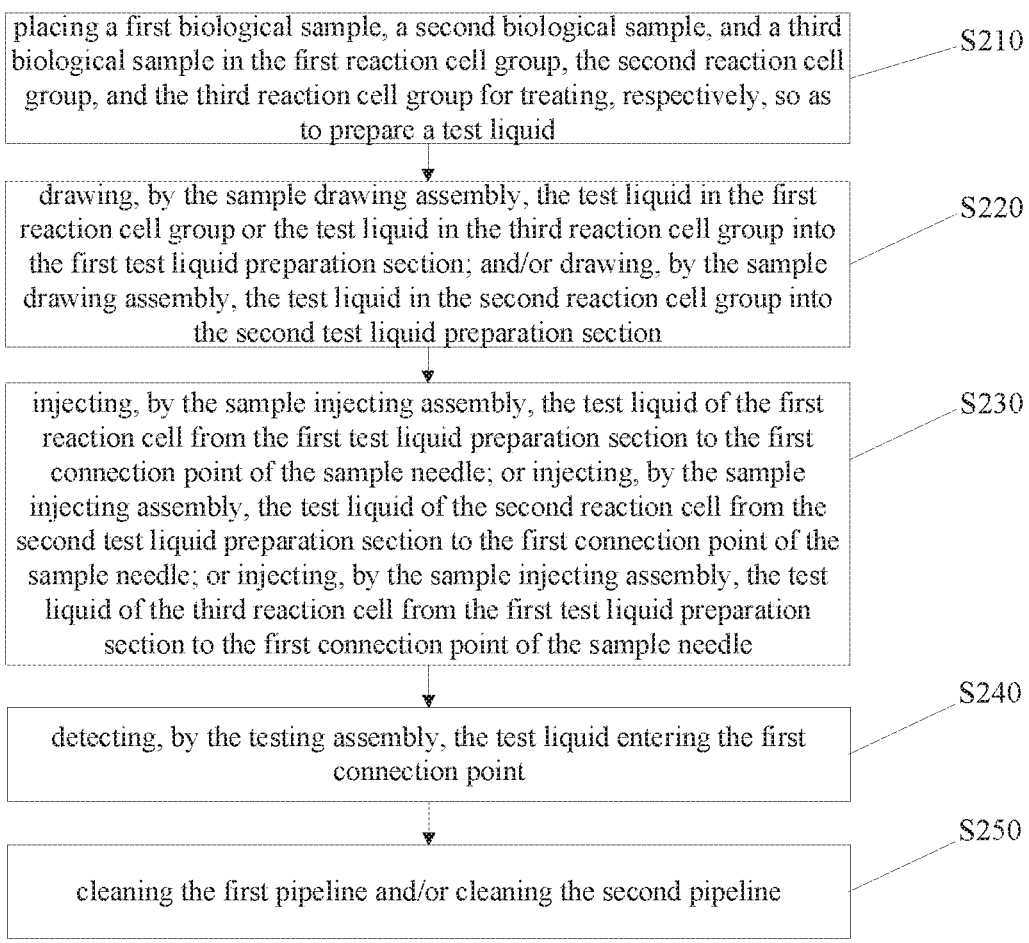
FIG. 14 is a flowchart of another sample testing method provided by an embodiment of the application.

Referring to FIGS. 11 and 14, an embodiment of the application further provides a sample testing method, where the sample detecting method is performed by using the sample testing device 200 provided by Embodiment, and the sample testing method includes the following steps.

S210: placing a first biological sample, a second biological sample, and a third biological sample in the first reaction cell group 231, the second reaction cell group 232, and the third reaction cell group 233 for treating, respectively, so as to prepare a test liquid.

Alternatively, the first biological sample and the third biological sample are different from the second biological sample, the first biological sample and the third biological sample are the same; or the first biological sample and the third biological sample are different from each other.

S220: drawing, by the sample drawing assembly 25, the test liquid in the first reaction cell group 231 or the test liquid in the third reaction cell group 233 into the first test liquid preparation section; and/or drawing, by the sample drawing assembly 25, the test liquid in the second reaction cell group 232 into the second test liquid preparation section.

Specifically, when drawing the first test liquid first and then drawing the second test liquid: the first switching member 2313, the fourth switching member 26 and the seventh switching member 252 are opened, so that the first test liquid in the first reaction cell 2311 is drawn into the first test liquid preparation section from the second connection point S2 under the negative pressure of the second waste liquid cell 251; and then, the fourth switching member 26 is closed and the eighth switching member 27 is opened, so that the second test liquid in the second reaction cell 2321 is drawn into the second test liquid preparation section from the second pipeline 212 under the negative pressure of the second waste liquid cell 251. The situation of drawing the second test liquid first is not to be described here again.

When drawing the third test liquid first and then drawing the second test liquid: the third switching member 2333, the fourth switching member 26 and the seventh switching member 252 are opened, so that the third test liquid in the third reaction cell 2331 is drawn from the sixth connection point S6 into the first test liquid preparation section under the negative pressure of the second waste liquid cell 251; and then the fourth switching member 26 is closed and the eighth switching member 27 is opened, so that the second test liquid in the second reaction cell 2321 is drawn into the second test liquid preparation section from the second pipeline 212 under the negative pressure of the second waste liquid cell 251. The situation of drawing the second test liquid first is not to be described here again.

When drawing the first test liquid and the second test liquid simultaneously, the first switching member 2313, the fourth switching member 26, the eighth switching member 27, and the seventh switching member 252 are opened, so that the first test liquid in the first reaction cell 2311 is drawn into the first test liquid preparation section from the second connection point S2 under the negative pressure of the second waste liquid cell 251, and the second test liquid in the second reaction cell 2321 is drawn into the second test liquid preparation section from the second pipeline 212 under the negative pressure of the second waste liquid cell 251.

When drawing the third test liquid and the second test liquid simultaneously, the third switching member 2333, the fourth switching member 26, the eighth switching member 27, and the seventh switching member 252 are opened, so that the third test liquid in the third reaction cell 2331 is drawn from the sixth connection point S6 into the first test liquid preparation section under the negative pressure of the second waste liquid cell 251, and the second test liquid in the second reaction cell 2321 is drawn into the second test liquid preparation section from the second pipeline 212 under the negative pressure of the second waste liquid cell 251.

The above four drawing situations are correspondingly performed according to actual needs, after the drawing of the test liquid is completed, the opened switching members are correspondingly closed for subsequent operations.

S230: injecting, by the sample injecting assembly 24, the test liquid of the first reaction cell 2311 from the first test liquid preparation section to the first connection point S1 of the sample needle 221; or injecting, by the sample injecting assembly 24, the test liquid of the second reaction cell 2321 from the second test liquid preparation section to the first connection point S1 of the sample needle 221; or injecting, by the sample injecting assembly 24, the test liquid of the third reaction cell 2331 from the first test liquid preparation section to the first connection point S1 of the sample needle 221.

Specifically, the first test liquid, the second test liquid, or the third test liquid are injected to the first connection point S1 according to actual needs, the process of injecting the first test liquid to the first connection point S1 is as follows: the selection switching member 242 is made to communicate with the fourth branch 243, and the injection liquid in the injector 241 is injected from the fourth branch 243 to the third connection point S3, and the first test liquid in the first test liquid preparation section is injected to the first connection point S1 to enter the flow chamber 222.

The process of injecting the second test liquid to the first connection point S1 is as follows: the selection switching member 242 is made to communicate with the fifth branch 244, and the injection liquid in the injector 241 is injected from the fifth branch 244 to the fourth connection point S4, and the second test liquid in the second test liquid preparation section is injected to the first connection point S1 to enter the flow chamber 222.

The process of injecting the third test liquid to the first connection point S1 is as follows: the selection switching member 242 is made to communicate with the fourth branch 243, and the injection liquid in the injector 241 is injected from the fourth branch 243 to the third connection point S3, and the third test liquid in the first test liquid preparation section is injected to the first connection point S1 and enters the flow chamber 222.

S240: detecting, by the testing assembly 22, the test liquid entering the first connection point S1.

Specifically, if the sample injecting assembly 24 injects the test liquid in the first reaction cell group 231 from the first test liquid preparation section to the first connection point S1 of the sample needle 221 in S230, the first test liquid is detected at a first time as follows: opening the fifth switching member 224 and the sixth switching member 226, so that the first test liquid enters the flow chamber 222 from the test liquid inlet 222a, and the sheath liquid in the sheath liquid cell 223 flows into the flow chamber 222 through the sheath liquid inlet 222b, and the sheath liquid surrounds the first test liquid to form a first test liquid flow for detecting, and finally the test liquid flow having been detected enters the first waste liquid cell 225 from the outlet 222c, and the detection of the first test liquid is completed.

If the sample injecting assembly 24 injects the test liquid in the second reaction cell group 232 from the second test liquid preparation section to the first connection point S1 of the sample needle 221 in S230, the second test liquid is detected at a second time as follows: opening the fifth switching member 224 and the sixth switching member 226, so that the second test liquid enters the flow chamber 222 from the test liquid inlet 222a, and the sheath liquid in the sheath liquid cell 223 flows into the flow chamber 222 via the sheath liquid inlet 222b, and the sheath liquid surrounds the second test liquid to form a second test liquid flow for detecting, and finally, the second test liquid flow having been detected enters the first waste liquid cell 225 from the outlet 222c, and the detection of the second test liquid is completed.

If the sample injecting assembly 24 injects the test liquid in the third reaction cell group 233 from the first test liquid preparation section to the first connection point S1 of the sample needle 221 in S230, the third test liquid is detected at a third time as follows: opening the fifth switching member 224 and the sixth switching member 226, so that the third test liquid enters the flow chamber 222 from the test liquid 222a inlet, and the sheath liquid in the sheath liquid cell 223 flows into the flow chamber 222 through the sheath liquid inlet 222b, and the sheath liquid surrounds the third test liquid to form a third test liquid flow for detecting, and finally, the test liquid flow having been detected enters the first waste liquid cell 225 from the outlet 222c, and the detection of the third test liquid is completed.

The above first time, the second time, and the third time are different from each other, that is, the testing assembly 22 detects the first test liquid, the second test liquid, and the third test liquid at different times respectively (time sharing).

S250: cleaning the first pipeline 211 and/or cleaning the second pipeline 212.

Alternatively, the cleaning assembly 28 (the first cleaning assembly 28, the second cleaning assembly 28, and the third cleaning assembly 28) includes a diluent and a cleaning liquid that is stronger than the diluent in cleaning. After each time a biological sample is detected, the pipeline corresponding to the biological sample is cleaned with the diluent to wash the blood sample in the pipeline after reaction. The cleaning action of the cleaning liquid may not be performed for each pipeline, and may be performed for a specific channel, or may be performed for a corresponding pipeline after detecting once, or may be performed for a certain pipeline after the certain pipeline has run for a certain number of times. For example, the first pipeline may be cleaned with the cleaning liquid after detecting the first test liquid, or the first pipeline may be cleaned with the cleaning liquid after the first pipeline has run for multiple detection times accumulatively; and the second pipeline may be cleaned with the cleaning liquid after detecting the second test liquid, or the second pipeline may be cleaned with the cleaning liquid after the second pipeline has run for multiple detection times accumulatively.

Specifically, the specific rinsing process for rinsing the first pipeline 211 using the cleaning liquid or the diluent is as follows: the fourth switching member 26 and the seventh switching member 252 are opened, and the cleaning liquid or the diluent enters the first pipeline 211 under the coaction of the positive pressure power of the cleaning liquid or the diluent and the negative pressure power of the sample drawing assembly 25 to rinse the first pipeline 211.

The specific rinsing process for rinsing the second pipeline 212 using the cleaning liquid or diluent is as follows: the eighth switching member 27 and the seventh switching member 252 are opened, and the cleaning liquid or the diluent enters the second pipeline 212 under the coaction of the positive pressure power of the cleaning liquid or the diluent and the negative pressure power of the sample drawing assembly 25 to rinse the second pipeline 212.

The sample testing method provided by the embodiment of the application can prevent cross-contamination and improve the accuracy of detection by making the second test liquid flow independently from other test liquids.

Figure 15:
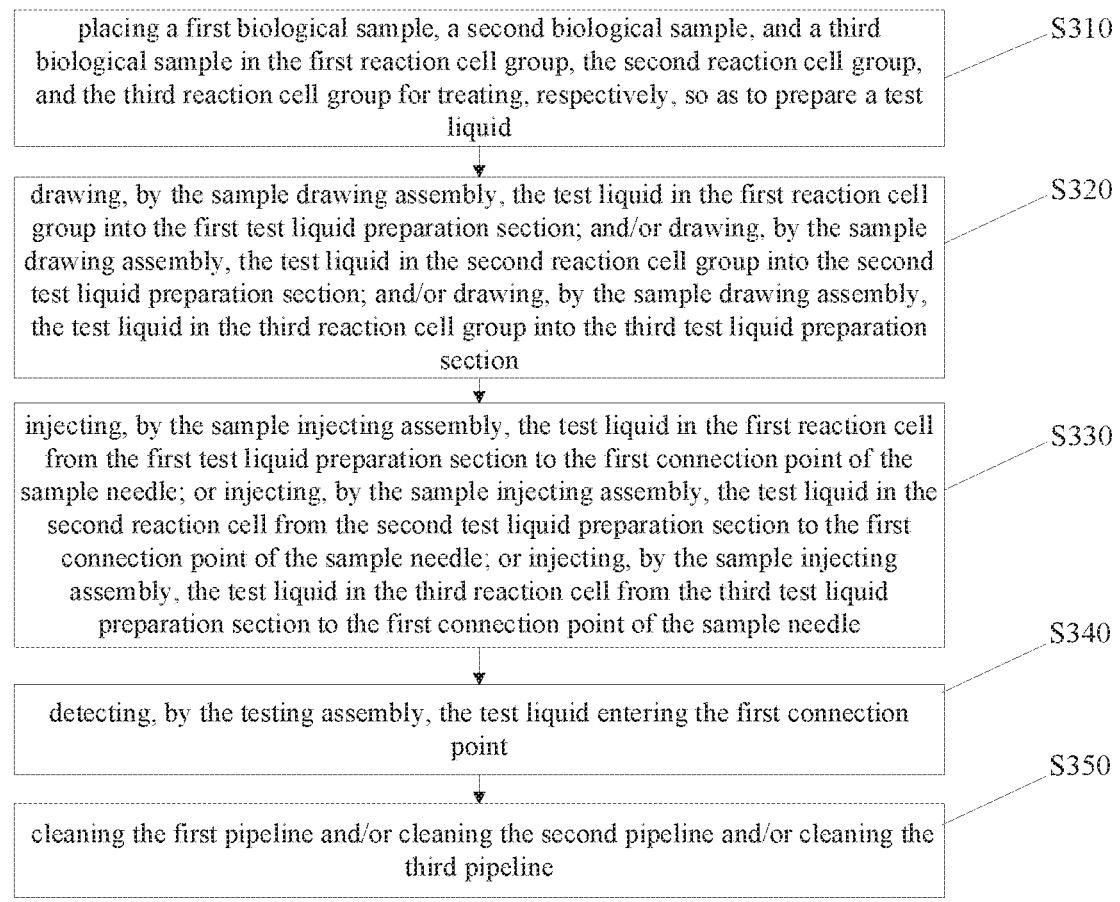
FIG. 15 is a flowchart of yet another sample testing method provided by an embodiment of the application.

Referring to FIGS. 12 and 15, an embodiment of the application further provides a sample testing method, the sample testing method is performed by using the sample testing device 300 provided by Embodiment and the sample testing method includes the following steps.

S310: placing a first biological sample, a second biological sample, and a third biological sample in the first reaction cell group 331, the second reaction cell group 332, and the third reaction cell group 333 for treating, respectively, so as to prepare a test liquid.

S320: drawing, by the sample drawing assembly 35, the test liquid in the first reaction cell group 331 into the first test liquid preparation section; and/or drawing, by the sample drawing assembly 35, the test liquid in the second reaction cell group 332 into the second test liquid preparation section; and/or drawing, by the sample drawing assembly 35, the test liquid in the third reaction cell group 333 into the third test liquid preparation section.

Specifically, when drawing the first test liquid, the second test liquid, and the third test liquid in sequence: the first switching member 3313, the fourth switching member 36 and the seventh switching member 352 are opened, so that the first test liquid in the first reaction cell 3311 is drawn into the first test liquid preparation section from the second connection point S2 under the negative pressure of the second waste liquid cell 351; then, the fourth switching member 36 is closed and the eighth switching member 37 is opened, so that the second test liquid in the second reaction cell 3321 is drawn into the second test liquid preparation section from the second pipeline 312 under the negative pressure of the second waste liquid cell 351; and then, the eighth switching member 37 is closed and the ninth switching member 39 is opened, so that the third test liquid in the third reaction cell 3331 is drawn into the third test liquid preparation section from the third pipeline 313 under the negative pressure of the second waste liquid cell 351. The drawing sequence of the first, second and third test liquids can be adjusted as needed, and will not be described again.

When drawing the first test liquid, the second test liquid, and the third test liquid simultaneously, the first switching member 3313, the fourth switching member 36, the second switching member 3323, the eighth switching member 37, the third switching member 3333, the ninth switching member 39, and the seventh switching member 352 are opened, so that the first test liquid in the first reaction cell 3311 is drawn into the first test liquid preparation section from the second connection point S2 under the negative pressure of the second waste liquid cell 351, the second test liquid in the second reaction cell 3321 is drawn into the second test liquid preparation section from the second pipeline 312 under the negative pressure of the second waste liquid cell 351, and the third test liquid in the third reaction cell 3331 is drawn into the third test liquid preparation section from the third pipeline 313 under the negative pressure of the second waste liquid cell 351.

The above four drawing situations are correspondingly performed according to actual needs, after the drawing of the test liquid is completed, the opened switching members are correspondingly closed for subsequent operations.

S330: injecting, by the sample injecting assembly 34, the test liquid in the first reaction cell 3311 from the first test liquid preparation section to the first connection point S1 of the sample needle 321; or injecting, by the sample injecting assembly 34, the test liquid in the second reaction cell 3321 from the second test liquid preparation section to the first connection point S1 of the sample needle 321; or injecting, by the sample injecting assembly 34, the test liquid in the third reaction cell 3331 from the third test liquid preparation section to the first connection point S1 of the sample needle 321.

Specifically, the first test liquid, the second test liquid, or the third test liquid are injected to the first connection point S1 according to actual needs, the process of injecting the first test liquid to the first connection point S1 is as follows: the selection switching member 342 is made to communicate with the fourth branch 343, and the injection liquid in the injector 341 is injected from the fourth branch 343 to the third connection point S3, and the first test liquid in the first test liquid preparation section is injected to the first connection point S1 to enter the flow chamber 322.

The process of injecting the second test liquid to the first connection point S1 is as follows: the selection switching member 342 is made to communicate with the fifth branch 344, and the injection liquid in the injector 341 is injected from the fifth branch 344 to the fourth connection point S4, and the second test liquid in the second test liquid preparation section is injected to the first connection point S1 to enter the flow chamber 322.

The process of injecting the third test liquid to the first connection point S1 is as follows: the selection switching member 342 is made to communicate with the sixth branch 345, and the injection liquid in the injector 341 is injected from the sixth branch 345 to the seventh connection point S7, and the third test liquid in the third test liquid preparation section is injected to the first connection point S1 and enters the flow chamber 322.

S340: detecting, by the testing assembly 32, the test liquid entering the first connection point S1.

Specifically, if the sample injecting assembly 34 injects the test liquid in the first reaction cell group 331 from the first test liquid preparation section to the first connection point S1 of the sample needle 321 in S330, the first test liquid is detected at a first time as follows: opening the fifth switching member 324 and the sixth switching member 326, so that the first test liquid enters the flow chamber 322 from the test liquid inlet 322a, and the sheath liquid in the sheath liquid cell 323 flows into the flow chamber 322 through the sheath liquid inlet 322b, and the sheath liquid surrounds the first test liquid to form a first test liquid flow for detecting, and finally, the test liquid flow having been detected enters the first waste liquid cell 325 from the outlet 322c, and the detection of the first test liquid is completed.

If the sample injecting assembly 34 injects the test liquid in the second reaction cell group 332 from the second test liquid preparation section to the first connection point S1 of the sample needle 321 in S330, the second test liquid is detected at a second time as follows: opening the fifth switching member 324 and the sixth switching member 326, so that the second test liquid enters the flow chamber 322 from the test liquid inlet 322a, and the sheath liquid in the sheath liquid cell 323 flows into the flow chamber 322 via the sheath liquid inlet 322b, and the sheath liquid surrounds the second test liquid to form a second test liquid flow for detecting, and finally, the second test liquid flow having been detected enters the first waste liquid cell 325 from the outlet 322c, and the detection of the second test liquid is completed.

If the sample injecting assembly 34 injects the test liquid in the third reaction cell group 333 from the third test liquid preparation section to the first connection point S1 of the sample needle 321 in S330, the third test liquid is detected at a third time as follows: opening the fifth switching member 324 and the sixth switching member 326, so that the third test liquid enters the flow chamber 322 from the test liquid inlet 322a, and the sheath liquid in the sheath liquid cell 323 flows into the flow chamber 322 via the sheath liquid inlet 322b, and the sheath liquid surrounds the third test liquid to form a third test liquid flow for detecting, and finally, the test liquid flow having been detected enters the first waste liquid cell 325 from the outlet 322c, and the detection of the third test liquid is completed.

The above first time, the second time, and the third time are different from each other, that is, the testing assembly 32 detects the first test liquid, the second test liquid, and the third test liquid at different times respectively (time sharing).

S350: cleaning the first pipeline 311 and/or cleaning the second pipeline 312 and/or cleaning the third pipeline 313.

Alternatively, after each time a biological sample is detected, the pipeline corresponding to the biological sample is cleaned with the diluent to wash the blood sample in the pipeline after the reaction. The cleaning action of the cleaning liquid may not be performed for each pipeline, and may be performed for a specific channel, or may be performed for a certain pipeline after the certain pipeline has run for a certain number of times.

The specific rinsing process for rinsing the first pipeline 311 using a cleaning liquid or diluent is as follows: the fourth switching member 36 and the seventh switching member 352 are opened, and the cleaning liquid or the diluent enters the first pipeline 311 under the coaction of the positive pressure power of the cleaning liquid or the diluent and the negative pressure power of the sample drawing assembly 35 to rinse the first pipeline 311.

The specific rinsing process for rinsing the second pipeline 312 using a cleaning liquid or diluent is: the eighth switching member 37 and the seventh switching member 352 are opened, and the cleaning liquid or the diluent enters the second pipeline 312 under the coaction of the positive pressure power of the cleaning liquid or the diluent and the negative pressure power of the sample drawing assembly 35 to rinse the second pipeline 312.

The specific rinsing process for rinsing the third pipeline 313 using a cleaning liquid or diluent is: the ninth switching member 39 and the seventh switching member 352 are opened, and the cleaning liquid or the diluent enters the third pipeline 313 under the coaction of the positive pressure power of the cleaning liquid or the diluent and the negative pressure power of the sample drawing assembly 35 to rinse the third pipeline 313.

The sample testing method provided by the embodiment of the application enables the first test liquid, the second test liquid, and the third test liquid to flow via different pipelines (corresponding to the first pipeline 311 and the second pipeline 312, the third pipeline 313, respectively) into the sample needle 321 of the testing assembly 32 for detecting, so that there is no interference with each other, which is advantageous for ensuring the accuracy of the detecting results of the testing assembly 32.

The embodiments of the disclosure have been described in detail above, and specific examples are used herein to explain the principles and implementation of the disclosed method and system. The above description of the embodiments is only used to facilitate understanding of the disclosed method and system and the core concept thereof. Moreover, for those skilled in the art, there can be modifications in the specific implementation and application scope based on the disclosed concept, and to sum up, the content of this specification should not be construed as limiting the claims,

What is claimed is:

1. A sample testing device, comprising:
a pipeline assembly which comprises a first pipeline and a second pipeline;
a testing assembly which comprises a sample needle, wherein the sample needle comprises a first connection point; and
a reaction assembly which comprises a first reaction cell group and a second reaction cell group, wherein the first reaction cell group is connected to a second connection point of the first pipeline, and the second reaction cell group communicates with the second pipeline, and the reaction assembly is configured to treat a biological sample to prepare a test liquid;
wherein a test liquid in the first reaction cell group flows to the first connection point of the sample needle via the second connection point of the first pipeline, and a test liquid in the second reaction cell group flows to the first connection point of the sample needle via the second pipeline, such that the test liquid in the first reaction cell group or in the second reaction cell group respectively flows into the sample needle of the testing assembly for detecting,
wherein the sample testing device further comprises a sample injecting assembly, the sample injecting assembly is respectively connected to a third connection point of the first pipeline and a fourth connection point of the second pipeline, the third connection point is located between the second connection point and the first connection point, a channel between the third connection point and the first connection point is configured as a first test liquid preparation section, and a channel between the fourth connection point and the first connection point is configured as a second test liquid preparation section,
wherein the test liquid in the first reaction cell group flows to the third connection point of the first pipeline via the second connection point of the first pipeline, and flows into the first test liquid preparation section via the third connection point of the first pipeline, wherein the test liquid in the second reaction cell group flows to the fourth connection point of the second pipeline via the second pipeline, and flows into the second test liquid preparation section via the fourth connection point of the second pipeline,
wherein the sample injecting assembly is configured to inject the test liquid in the first test liquid preparation section or in the second test liquid preparation section into the sample needle of the testing assembly,
wherein an end of the second pipeline away from the second reaction cell group is connected to a tenth connection point of the first pipeline, and the tenth connection point and the second connection point are respectively located on opposite sides of the first connection point, and
wherein a three-way joint is provided on the first pipeline for communicating the tenth connection point and the second connection point with the first connection point of the sample needle.

2. The sample testing device of claim 1, wherein the sample testing device further comprises a sample drawing assembly, the sample drawing assembly is connected to an end of the first pipeline or the end of the second pipeline, and the sample drawing assembly is configured to generate a negative pressure to correspondingly draw the test liquid in the first reaction cell group into the first test liquid preparation section, or draw the test liquid in the second reaction cell group into the second test liquid preparation section.

3. The sample testing device of claim 2, wherein the sample drawing assembly comprises a second waste liquid cell and a seventh switching member; a negative pressure is generated in the second waste liquid cell, and the seventh switching member is connected between the second waste liquid cell and an end of the first pipeline, the end of the second pipeline or an end of a third pipeline, and the seventh switching member is configured to implement cutting-off and connecting.

4. The sample testing device of claim 1, wherein the sample testing device further comprises a first cleaning assembly and a second cleaning assembly, the first cleaning assembly is connected to the first pipeline, and a cleaning fluid in the first cleaning assembly flows into the first pipeline to clean the first pipeline, and
wherein the second cleaning assembly is connected to the second pipeline, and a cleaning fluid in the second cleaning assembly flows into the second pipeline to clean the second pipeline.

5. The sample testing device of claim 1, wherein the sample testing device comprises a third cleaning assembly, the first pipeline and the second pipeline are commonly connected to the third cleaning assembly, and a cleaning fluid in the third cleaning assembly flows into the first pipeline or the second pipeline to clean the first pipeline or the second pipeline.

6. The sample testing device of claim 5, wherein the second reaction cell group is further connected to a fifth connection point of the first pipeline, and the third cleaning assembly is connected to an end of the first pipeline,
wherein the cleaning fluid in the third cleaning assembly flows into the first pipeline from the end of the first pipeline to clean the first pipeline, or the cleaning fluid in the third cleaning assembly flows from the end of the first pipeline to the fifth connection point of the first pipeline, and flows from the fifth connection point into the connection point of the second reaction cell group in the second pipeline to clean the second pipeline.

7. The sample testing device of claim 1, wherein the reaction assembly further comprises a third reaction cell group, the third reaction cell group is connected to a sixth connection point of the first pipeline, and a test liquid in the third reaction cell group flows to the first connection point of the sample needle via the sixth connection point of the first pipeline, so that the test liquid in the third reaction cell group flows into the sample needle of the testing assembly for detecting,
wherein the test liquid in the first reaction cell group or the third reaction cell group respectively flows to the third connection point of the first pipeline via the second connection point of the first pipeline or the sixth connection point of the first pipeline, and flows into the first test liquid preparation section via the third connection point of the first pipeline, or the test liquid in the second reaction cell group flows to the fourth connection point of the second pipeline via the second pipeline, and flows into the second test liquid preparation section via the fourth connection point of the second pipeline.

8. The sample testing device of claim 1, wherein the sample injecting assembly comprises an injector, a selection switching member disposed at an injection port of the injector, a fourth branch and a fifth branch; one end of the fourth branch and one end of the fifth branch are respectively connected to the third connection point and the fourth connection point, another end of the fourth branch and another end of the fifth branch are commonly disposed at the selection switching member, and the selection switching member is configured to switch between the fourth branch and the fifth branch to communication with the injector.

9. The sample testing device of claim 8, wherein the sample testing device further comprises a sample drawing assembly, the sample drawing assembly is connected to an end of the first pipeline or the end of the second pipeline, and the sample drawing assembly is configured to:
generate a negative pressure to draw the test liquid in the first reaction cell group or in the third reaction cell group into the first test liquid preparation section; or
generate a negative pressure to draw the test liquid in the second reaction cell group into the second test liquid preparation section.

10. The sample testing device of claim 1, wherein the pipeline assembly further comprises a third pipeline, the reaction assembly further comprises a third reaction cell group, and the third reaction cell group communicates with the third pipeline; and a test liquid in the third reaction cell group flows to the first connection point of the sample needle via the third pipeline, so that the test liquid in the third reaction cell group flows into the sample needle of the testing assembly for detecting.

11. The sample testing device of claim 10, wherein the sample injecting assembly is further connected to a seventh connection point of the third pipeline, and a channel between the seventh connection point and the first connection point is a third test liquid preparation section,
wherein the test liquid in the third reaction cell group flows via the third pipeline to the seventh connection point of the third pipeline, and flows into the third test liquid preparation section via the seventh connection point of the third pipeline,
wherein the sample injecting assembly is configured to inject the test liquid in the first test liquid preparation section, the test liquid in the second test liquid preparation section or the test liquid in the third test liquid preparation section into the sample needle of the testing assembly.

12. The sample testing device of claim 11, wherein the sample injecting assembly comprises an injector, a selection switching member disposed at an injection port of the injector, a fourth branch, a fifth branch and a sixth branch; one end of the fourth branch, one end of the fifth branch and one end of the sixth branch are respectively connected to the third connection point, the fourth connection point and the seventh connection point, another end of the fourth branch, another end of the fifth branch and another end of the sixth branch are commonly disposed at the selection switching member, and the selection switching member is configured to switch between the fourth branch, the fifth branch and the sixth branch to communication with the injector.

13. The sample testing device of claim 11, wherein the sample testing device further comprises a sample drawing assembly, the sample drawing assembly is connected to an end of the first pipeline, the end of the second pipeline, or an end of the third pipeline, and the sample drawing assembly is configured to generate a negative pressure to correspondingly draw the test liquid in the first reaction cell group into the first test liquid preparation section, or draw the test liquid in the second reaction cell group into the second test liquid preparation section, or draw the test liquid in the third reaction cell group into the third test liquid preparation section.

14. The sample testing device of claim 1, wherein the second cell group is directly connected to the second pipeline; or,
wherein the second reaction cell group is connected to the second pipeline indirectly via the first pipeline.

15. The sample testing device of claim 1, wherein the second reaction cell group is further connected to a fifth connection point of the first pipeline, and the second pipeline is connected to an eighth connection point of the first pipeline, the test liquid in the second reaction cell group flows from the fifth connection point to the eighth connection point, and flows into the second pipeline from the eighth connection point such that the second reaction cell group communicates with the second pipeline; or,
wherein the second reaction cell group is further connected to a fifth connection point of the first pipeline, the test liquid in the first reaction cell group flows from the second connection point to the eighth connection point, and flows from the eighth connection point to the first connection point; the second pipeline is connected to the eighth connection point of the first pipeline, and the test liquid in the second reaction cell group flows from the fifth connection point to the eighth connection point, and flows into the second pipeline from the eighth connection point such that the second reaction cell group communicates with the second pipeline; or,
wherein the second pipeline and the second reaction cell group are commonly connected to the fifth connection point of the first pipeline, and the test liquid in the second reaction cell group flows into the second pipeline from the fifth connection point such that the second reaction cell group communicates with the second pipeline.

16. The sample testing device of claim 1, wherein the test liquid in the second reaction cell group flows to the tenth connection point of the first pipeline via the second pipeline, and flows from the tenth connection point of the first pipeline to the first connection point of the sample needle.

17. The sample testing device of claim 16, wherein the test liquid in the first reaction cell group does not flow through the tenth connection point of the first pipeline when flowing from the second connection point of the first pipeline to the first connection point of the sample needle.

18. The sample testing device of claim 1, wherein the first reaction cell group comprises a first reaction cell, a first branch, and a first switching member; the first reaction cell is configured to prepare a first test liquid, the first branch is connected between the first reaction cell and the second connection point, and the first switching member is disposed in the first branch and is configured to implement cutting-off and connecting of the first branch; and
wherein the second reaction cell group comprises a second reaction cell, a second branch, and a second switching member, wherein the second reaction cell is configured to prepare a second test liquid, one end of the second branch is connected to the second reaction cell, the second branch communicates with the second pipeline, and the second switching member is disposed in the second branch and is configured to implement cutting-off or connecting of the second branch.

19. The sample testing device of claim 1, wherein the testing assembly further comprises a flow chamber, a sheath liquid cell, a fifth switching member, a first waste liquid cell, and a sixth switching member,
wherein the flow chamber has an test liquid inlet, a sheath liquid inlet, and an outlet,
wherein the test liquid inlet is connected to the first connection point of the sample needle, and the sheath liquid inlet is connected to the sheath liquid cell,
wherein the sheath liquid cell is configured to store a sheath liquid, the fifth switching member is connected between the sheath liquid cell and the sheath liquid inlet, and the fifth switching member is configured to implement cutting-off and connecting,
wherein the outlet is connected to the first waste liquid cell, the sixth switching member is connected between the first waste liquid cell and the outlet, and the sixth switching member is configured to implement cutting-off and connecting.

20. The sample testing device of claim 1, wherein the sample testing device further comprises a fourth switching member, the fourth switching member is disposed in the first pipeline, and the fourth switching member is located between the third connection point and the second connection point and is configured to implement cutting-off or connecting; and
wherein an eighth switching member is disposed in the second pipeline, and the eighth switching member is located between the fourth connection point and the second pipeline and is configured to implement cutting-off or connecting.

21. The sample testing device of claim 1, wherein the first reaction cell group is configured to prepare the first test liquid for counting leukocytes, the second reaction cell group is configured to prepare the second test liquid for counting reticulocytes.

22. A sample testing method, which is performed by using the sample testing device of claim 1, comprising:
placing a first biological sample and a second biological sample in the first reaction cell group and the second reaction cell group for treating, respectively, so as to prepare a test liquid;
flowing the test liquid in the first reaction cell group to the third connection point of the first pipeline via the second connection point of the first pipeline, and further into the first test liquid preparation section via the third connection point of the first pipeline, and injecting, by the sample injecting assembly, the test liquid from the first test liquid preparation section into the first connection point of the sample needle, and detecting, by the testing assembly, the test liquid in the first reaction cell group which flows to the first connection point of the sample needle at a first time; and
flowing the test liquid in the second reaction cell group to the fourth connection point of the second pipeline via the second pipeline, and further into the second test liquid preparation section via the fourth connection point of the second pipeline, and injecting, by the sample injecting assembly, the test liquid from the second test liquid preparation section into the first connection point of the sample needle, and detecting, by the testing assembly, the test liquid in the second reaction cell group which flows to the first connection point of the sample needle at a second time.

23. The method of claim 22, wherein the sample testing device further comprises a sample drawing assembly, and the sample drawing assembly is connected to an end of the first pipeline or an end of the second pipeline,
  wherein the flowing the test liquid in the first reaction cell group to the first connection point of the sample needle via the second connection point of the first pipeline further comprises: firstly drawing, by the sample drawing assembly, the test liquid from the first reaction cell group into the first test liquid preparation section, and then injecting, by the sample injecting assembly, the test liquid from the first test liquid preparation section into the first connection point of the sample needle, and
  wherein the flowing the test liquid in the second reaction cell group to the first connection point of the sample needle via the second pipeline comprises: firstly drawing, by the sample drawing assembly, the test liquid from the second reaction cell group into the second test liquid preparation section, and then injecting, by the sample injecting assembly, the test liquid from the second test liquid preparation section into the first connection point of the sample needle.

24. The method of claim 22, wherein the method further comprises:
  after detecting the test liquid in the first reaction cell group by the testing assembly, cleaning the first pipeline; or
  after detecting the test liquid in the second reaction cell group by the testing assembly, cleaning the second pipeline.

25. The method of claim 22, wherein the sample testing device further comprises a controller, and the controller is configured to count a number of times that the testing assembly tests the test liquid in the first reaction cell group and a number of times that the testing assembly tests the test liquid in the second reaction cell group, and determine whether the counted numbers of times reach a preset test number,
  wherein the method further comprises:
  cleaning the first pipeline after the testing assembly has performed the preset test number of tests on the test liquid in the first reaction cell group; or
  cleaning the second pipeline after the testing assembly has performed the preset test number of tests on the test liquid in the second reaction cell group.

26. The method of claim 22, wherein the reaction assembly further comprises a third reaction cell group, the third reaction cell group is connected to a sixth connection point of the first pipeline, and a test liquid in the third reaction cell group flows to the first connection point of the sample needle via the sixth connection point of the first pipeline,
  wherein and the sample testing method further comprises:
  placing a third biological sample in the third reaction cell group for treating, so as to generate a test liquid; and
  flowing the test liquid in the third reaction cell group to the third connection point of the first pipeline via the sixth connection point of the first pipeline, and further into the first test liquid preparation section via the third connection point of the first pipeline, and injecting, by the sample injecting assembly, the test liquid from the first test liquid preparation section to the first connection point of the sample needle, and detecting, by the testing assembly, the test liquid of the third reaction cell group which flows to the first connection point of the sample needle at a third time.

27. The method of claim 26, wherein the sample testing device further comprises a sample drawing assembly, and the sample drawing assembly is connected to an end of the first pipeline or an end of the second pipeline,
  wherein the flowing the test liquid in the first reaction cell group to the first connection point of the sample needle via the second connection point of the first pipeline further comprises: firstly drawing, by the sample drawing assembly, the test liquid from the first reaction cell group into the first test liquid preparation section, and then injecting, by the sample injecting assembly, the test liquid from the first test liquid preparation section into the first connection point of the sample needle,
  wherein the flowing the test liquid in the second reaction cell group to the first connection point of the sample needle via the second pipeline comprises: firstly drawing, by the sample drawing assembly, the test liquid from the second reaction cell group into the second test liquid preparation section, and then injecting, by the sample injecting assembly, the test liquid from the second test liquid preparation section into the first connection point of the sample needle, and
  wherein the flowing the test liquid in the third reaction cell group to the first connection point of the sample needle via the sixth connection point of the first pipeline further comprises: firstly drawing, by the sample drawing assembly, the test liquid in the third reaction cell group into the first test liquid preparation section by generating a negative pressure, and then injecting, by the sample drawing assembly, the test liquid from the first test liquid preparation section to the first connection point of the sample needle.

28. The method of claim 22, wherein the pipeline assembly further comprises a third pipeline, the reaction assembly further comprises a third reaction cell group, and the third reaction cell group communicates with the third pipeline,
  wherein a test liquid in the third reaction cell group flows to the first connection point of the sample needle via the third pipeline; the sample injecting assembly is further connected to the seventh connection point of the third pipeline, and a channel between the seventh connection point and the first connection point is a third test liquid preparation section,
  wherein the sample testing method further comprises:
  placing a third biological sample in the third reaction cell group for treating, so as to prepare a test liquid; and
  flowing the test liquid in the third reaction cell group to the seventh connection point of the third pipeline via the third pipeline, and further into the third test liquid preparation section via the seventh connection point of the third pipeline, and injecting, by the sample injecting assembly, the test liquid from the third test liquid preparation section to the first connection point of the sample needle, and detecting, by the testing assembly, the test liquid of the third reaction cell group which flows to the first connection point of the sample needle at a third time.

29. The method of claim 28, wherein the sample testing device further comprises a sample drawing assembly, and the sample drawing assembly is connected to an end of the first pipeline or an end of the second pipeline or an end of the third pipeline,
  wherein the flowing the test liquid in the first reaction cell group to the first connection point of the sample needle via the second connection point of the first pipeline further comprises: firstly drawing, by the sample drawing assembly, the test liquid from the first reaction cell group into the first test liquid preparation section, and then injecting, by the sample injecting assembly, the test liquid from the first test liquid preparation section into the first connection point of the sample needle, wherein the flowing the test liquid in the second reaction cell group to the first connection point of the sample needle via the second pipeline comprises: firstly drawing, by the sample drawing assembly, the test liquid from the second reaction cell group into the second test liquid preparation section, and then injecting, by the sample injecting assembly, the test liquid from the second test liquid preparation section into the first connection point of the sample needle, wherein the flowing the test liquid in the third reaction cell group to the first connection point of the sample needle via the third pipeline further comprises: firstly drawing, by the sample drawing assembly, the test liquid in the third reaction cell group into the third test liquid preparation section by generating a negative pressure, and then injecting, by the sample injecting assembly, the test liquid from the third test liquid preparation section to the first connection point of the sample needle.

30. A sample analyzer, comprising:
a sampling assembly; and
a sample testing device,
wherein the sampling assembly comprises a sampler which is configured to collect a biological sample and move to a position above a reaction assembly to dispense the biological sample into the reaction assembly, and wherein the sample testing device comprising:
a pipeline assembly which comprises a first pipeline and a second pipeline;
a testing assembly which comprises a sample needle, wherein the sample needle comprises a first connection point; and
a reaction assembly which comprises a first reaction cell group and a second reaction cell group, wherein the first reaction cell group is connected to a second connection point of the first pipeline, and the second reaction cell group communicates with the second pipeline, and the reaction assembly is configured to treat a biological sample to prepare a test liquid;

wherein a test liquid in the first reaction cell group flows to the first connection point of the sample needle via the second connection point of the first pipeline, and a test liquid in the second reaction cell group flows to the first connection point of the sample needle via the second pipeline, such that the test liquid in the first reaction cell group or in the second reaction cell group respectively flows into the sample needle of the testing assembly for detecting, wherein the sample testing device further comprises a sample injecting assembly, the sample injecting assembly is respectively connected to a third connection point of the first pipeline and a fourth connection point of the second pipeline, the third connection point is located between the second connection point and the first connection point, a channel between the third connection point and the first connection point is configured as a first test liquid preparation section, and a channel between the fourth connection point and the first connection point is configured as a second test liquid preparation section, wherein the test liquid in the first reaction cell group flows to the third connection point of the first pipeline via the second connection point of the first pipeline, and flows into the first test liquid preparation section via the third connection point of the first pipeline, wherein the test liquid in the second reaction cell group flows to the fourth connection point of the second pipeline via the second pipeline, and flows into the second test liquid preparation section via the fourth connection point of the second pipeline, wherein the sample injecting assembly is configured to inject the test liquid in the first test liquid preparation section or in the second test liquid preparation section into the sample needle of the testing assembly, wherein an end of the second pipeline away from the second reaction cell group is connected to a tenth connection point of the first pipeline, and the tenth connection point and the second connection point are respectively located on opposite sides of the first connection point, and wherein a three-way joint is provided on the first pipeline for communicating the tenth connection point and the second connection point with the first connection point of the sample needle.

* * * * *